United States Patent
Thaxton et al.

(10) Patent No.: US 10,517,924 B2
(45) Date of Patent: Dec. 31, 2019

(54) HIGH DENSITY LIPOPROTEIN NANOPARTICLES FOR INFLAMMATION

(71) Applicant: Northwestern University, Evanston, IL (US)

(72) Inventors: C. Shad Thaxton, Chicago, IL (US); Linda Foit, Chicago, IL (US)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 15/529,214

(22) PCT Filed: Nov. 24, 2015

(86) PCT No.: PCT/US2015/062431
§ 371 (c)(1),
(2) Date: May 24, 2017

(87) PCT Pub. No.: WO2016/085986
PCT Pub. Date: Jun. 2, 2016

(65) Prior Publication Data
US 2017/0354711 A1 Dec. 14, 2017

Related U.S. Application Data

(60) Provisional application No. 62/083,864, filed on Nov. 24, 2014.

(51) Int. Cl.
| | | |
|---|---|---|
| *A61K 38/00* | (2006.01) | |
| *A61K 38/17* | (2006.01) | |
| *A61K 9/127* | (2006.01) | |
| *A61K 9/51* | (2006.01) | |
| *A61K 47/69* | (2017.01) | |
| *A61K 31/685* | (2006.01) | |
| *A61K 9/14* | (2006.01) | |
| *B82Y 5/00* | (2011.01) | |

(52) U.S. Cl.
CPC .......... *A61K 38/1709* (2013.01); *A61K 9/127* (2013.01); *A61K 9/14* (2013.01); *A61K 9/5115* (2013.01); *A61K 9/5184* (2013.01); *A61K 31/685* (2013.01); *A61K 47/6917* (2017.08); *B82Y 5/00* (2013.01)

(58) Field of Classification Search
CPC ............ A61K 38/1709; A61K 2300/00; A61K 31/685; A61K 47/6917; A61K 9/127; A61K 9/14; A61K 9/5115; A61K 9/5184; A61K 47/48838; B82Y 5/00
See application file for complete search history.

(56) References Cited

U.S. PATENT DOCUMENTS

| | | | |
|---|---|---|---|
| 5,264,618 A | 11/1993 | Felgner et al. | |
| 5,472,881 A | 12/1995 | Beebe et al. | |
| 6,361,944 B1 | 3/2002 | Mirkin et al. | |
| 8,323,686 B2 | 12/2012 | Mirkin et al. | |
| 9,532,948 B2 | 1/2017 | Mirkin et al. | |
| 9,693,957 B2 | 7/2017 | Lin et al. | |
| 2002/0172711 A1 | 11/2002 | Martin et al. | |
| 2004/0038891 A1* | 2/2004 | Bisgaier ............... A61K 9/1275 514/13.7 |
| 2004/0170560 A1 | 9/2004 | Fossheim et al. | |
| 2008/0181928 A1 | 7/2008 | Hakimi-Mehr et al. | |
| 2008/0194463 A1 | 8/2008 | Weller et al. | |
| 2008/0306016 A1 | 12/2008 | Mirkin et al. | |
| 2009/0209629 A1 | 8/2009 | Mirkin et al. | |
| 2009/0324706 A1 | 12/2009 | Mirkin et al. | |
| 2010/0136682 A1 | 6/2010 | Mirkin et al. | |
| 2010/0184844 A1 | 7/2010 | Mirkin et al. | |
| 2010/0233270 A1 | 9/2010 | Mirkin et al. | |
| 2011/0020242 A1 | 1/2011 | Zheng et al. | |
| 2011/0111974 A1 | 5/2011 | Mirkin et al. | |
| 2011/0256224 A1* | 10/2011 | Sigalov ............. A61K 51/1224 424/489 |
| 2013/0034599 A1 | 2/2013 | Thaxton et al. | |
| 2014/0294927 A1 | 10/2014 | Thaxton et al. | |
| 2016/0194642 A1 | 7/2016 | Gryaznov et al. | |
| 2016/0310425 A1 | 10/2016 | Mirkin et al. | |

FOREIGN PATENT DOCUMENTS

| | | | |
|---|---|---|---|
| WO | WO 95/34289 | * 12/1995 | ............. A61K 38/00 |
| WO | WO 95/034289 A1 | 12/1995 | |
| WO | WO 2005/063201 A2 | 7/2005 | |
| WO | WO 2005/063288 A1 | 7/2005 | |
| WO | WO 2008/014979 A2 | 2/2008 | |
| WO | WO 2009/051451 A2 | 4/2009 | |
| WO | WO 2009/073984 A1 | 6/2009 | |
| WO | WO 2009/131704 | 10/2009 | |
| WO | WO 2010/091293 A1 | 8/2010 | |
| WO | WO 2010/148249 A1 | 12/2010 | |
| WO | WO 2011/044545 A2 | 4/2011 | |

(Continued)

OTHER PUBLICATIONS

Akhter et al., Gold nanoparticles in theranostic oncology: current state-of-the-art. Expert Opin Drug Deliv. Oct. 2012;9(10):1225-43. Epub Aug. 16, 2012.

Banga et al., Liposomal spherical nucleic acids. J Am Chem Soc. Jul. 16, 2014;136(28):9866-9. doi: 10.1021/ja504845f. Epub Jul. 1, 2014.

Chromy et al., Different Apolipoproteins Impact Nanolipoprotein Particle Formation. J. Am. Chem. Soc., 2007;129(46):14348-14354.

Cormode et al., Nanocrystal Core High-Density Lipoproteins: A Multimodality Contrast Agent Platform. Nano Lett., 2008;8(11):3715-3723.

Frias, J. C. et al., Recombinant HDL-Like Nanoparticles: A Specific Contrast Agent for MRI of Atherosclerotic Plaques, J. Am. Chem. Soc., 2004, 126 (50), 16316-16317.

(Continued)

*Primary Examiner* — Thomas S Heard
(74) *Attorney, Agent, or Firm* — Wolf, Greenfield & Sacks, P.C.

(57) ABSTRACT

The invention in aspects relates to methods of treating sepsis using HDL-NP. The methods include the use of nanoparticles having a core and a lipid based shell with optimal lipids therein.

23 Claims, 10 Drawing Sheets

(56) References Cited

FOREIGN PATENT DOCUMENTS

| WO | WO 2013/151771 A1 | 10/2013 |
|----|-------------------|---------|
| WO | WO 2015/187966 A1 | 12/2015 |
| WO | WO 2017/011662 A1 | 1/2017 |
| WO | WO 2017/193087 A1 | 11/2017 |
| WO | WO 2018/053368 A1 | 3/2018 |

OTHER PUBLICATIONS

Giljohann et al., Gold nanoparticles for biology and medicine. Angew Chem Int Ed Engl. Apr. 26, 2010;49(19):3280-94. doi: 10.1002/anie.200904359.

Giljohann et al., Oligonucleotide loading determines cellular uptake of DNA-modified gold nanoparticles. Nano Lett. Dec. 2007;7(12):3818-21. Epub Nov. 13, 2007.

Gissot et al., Nucleoside, nucleotide and oligonucleotide based amphiphiles: a successful marriage of nucleic acids with lipids. Org. Biomol. Chem. 2008;6:1324-33.

Han et al., Drug and gene delivery using gold nanoparticles. NanoBiotechnology. Mar. 2007;3(1):40-5.

Hurst et al., Maximizing DNA Loading on a Range of Gold Nanoparticle Sizes. Anal. Chem. 2006;78(24):8313-8318.

Jones, Simultaneous labeling of lipoprotein intracellular trafficking in pigeon monocyte-derived macrophages. Am J Pathol. Mar. 1997;150(3):1113-24.

Kim et al., Cationic solid lipid nanoparticles reconstituted from low density lipoprotein components for delivery of siRNA. Mol Pharm. Jul.-Aug. 2008;5(4):622-31. doi: 10.1021/mp8000233. Epub May 8, 2008.

Kong et al., Cationic lipid-coated gold nanoparticles as efficient and non-cytotoxic intracellular siRNA delivery vehicles. Pharm Res. Feb. 2012;29(2):362-74. doi: 10.1007/s11095-011-0554-y. Epub Aug. 13, 2011.

Lin et al., Gold nanoparticle delivery of modified CpG stimulates macrophages and inhibits tumor growth for enhanced immunotherapy. PLoS One. May 15, 2013;8(5):e63550. doi: 10.1371/journal.pone.0063550. Print 2013.

Luthi et al., Nanotechnology for synthetic high-density lipoproteins. Trens Mol Med. Dec. 2010;16(12):553-60. doi: 10.1016/j.molmed.2010.10.006. Epub Nov. 17, 2010.

Luthi et al., Tailoring of biomimetic high-density lipoprotein nanostructures changes cholesterol binding and efflux. ACS Nano. Jan. 24, 2012;6(1):276-85. doi: 10.1021/nn2035457. Epub Dec. 1, 2011.

Lytton-Jean et al., A thermodynamic investigation into the binding properties of DNA functionalized gold nanoparticle probes and molecular fluorophore probes. J Am Chem Soc. Sep. 21, 2005;127(37):12754-5.

Massich et al., Regulating immune response using polyvalent nucleic acid-gold nanoparticle conjugates. Mol Pharm. Nov.-Dec. 2009;6(6):1934-40.

McMahon et al., Biomimetic high density lipoprotein nanoparticles for nucleic acid delivery. Nano Lett. Mar. 9, 2011;11(3):1208-14. doi: 10.1021/nl1041947. Epub Feb. 14, 2011.

Mirza et al., Preparation and characterization of doxorubicin functionalized gold nanoparticles. Eur J Med Chem. May 2011;46(5):1857-60. doi: 10.1016/j.ejmech.2011.02.048. Epub Feb. 24, 2011.

Niemeyer, C. et al., Bifunctional DNA-Gold Nanoparticle Conjugates as Building Blocks for the Self-Assembly of Cross-Linked Particle Layers. Biochemical Biophysical Research Communications. 2003;311(4):995-999.

Patel et al., Peptide antisense nanoparticles. Proc Natl Acad Sci U S A. Nov. 11, 2008;105(45):17222-6. doi: 10.1073/pnas.0801609105.

Patwa et al., Hybrid lipid oligonucleotide conjugates: synthesis, self-assemblies and biomedical applications. Chem Soc Rev. 2011;40:5844-54.

Paul, New Way to Kill Lymphoma without Chemotherapy uses Golden Nanoparticles. Feinberg School of Medicine: Northwestern University. Jan. 22, 2013. 4 pages. ww.feinberg.northwestern.edu/news/2013/01/lymphoma_nanoparticales.html.

Radovic-Moreno et al., Immunomodulatory spherical nucleic acids. Proc Natl Acad Sci U S A. Mar. 31, 2015;112(13):3892-7. doi: 10.1073/pnas.1502850112. Mar. 16, 2015.

Rana et al., Monolayer coated gold nanoparticles for delivery applications. Adv Drug Deliv Rev. Feb. 2012;64(2):200-16. doi: 10.1016/j.addr.2011.08.006. Epub Sep. 6, 2011.

Rosi et al., Oligonucleotide-modified gold nanoparticles for intracellular gene regulation. Science. May 19, 2006;312(5776):1027-30.

Thompson et al., Smart lipids for programmable nanomaterials. Nano Lett. Jul. 14, 2010;10(7):2690-3. doi: 10.1021/nl101640k.

Tiwari et al., Functionalized gold nanoparticles and their biomedical applications. Nanomaterials. 2011;1:31-63. doi: 10.3390/nano1010031.

Wolfrum et al., Mechanisms and optimization of in vivo delivery of lipophilic siRNAs. Nat Biotechnol. Oct. 2007;25(10):1149-57. Epub Sep. 16, 2007.

Yang et al., Biomimetic, synthetic HDL nanostructures for lymphoma. Proc Natl Acad Sci U S A. Feb. 12, 2013;110(7):2511-6. doi: 10.1073/pnas.1213657110. Epub Jan. 23, 2013.

Zhang et al., Informational liposomes: Complexes derived from cholesteryl-conjugated oligonucleotides and liposomes. Tetrahedron Letters. 1996. 37(35):6243-6.

Zheng et al., Topical delivery of siRNA-based spherical nucleic acid nanoparticle conjugates for gene regulation. Proc Natl Acad Sci U S A. Jul. 24, 2012;109(30):11975-80. doi: 10.1073/pnas.1118425109. Epub Jul. 6, 2012.

PCT/US2015/062431, Feb. 25, 2016, International Search Report and Written Opinion.

* cited by examiner

HIGH DENSITY LIPOPROTEIN NANOPARTICLES FOR INFLAMMATION

RELATED APPLICATIONS

This application is a national stage filing under U.S.C. § 371 of PCT International Application PCT/US2015/062431, entitled "HIGH DENSITY LIPOPROTEIN NANOPARTICLES FOR INFLAMMATION," filed Nov. 24, 2015, which claims priority under 35 U.S.C. § 119(e) to U.S. Provisional Application Ser. No. 62/083,864, entitled "HIGH DENSITY LIPOPROTEIN NANOPARTICLES FOR INFLAMMATION" filed on Nov. 24, 2014, which are herein incorporated by reference in their entirety.

GOVERNMENT SUPPORT

This invention was made with government support under grant number FA9550-13-1-0192 awarded by the Air Force Office of Scientific Research. The government has certain rights in the invention.

BACKGROUND OF INVENTION

Bacterial sepsis is a systemic inflammatory response to a severe bacterial infection and can, depending on severity, be accompanied by fever, hypotension, disseminated intravascular coagulation, and multiple organ failure. Sepsis is caused by cytokines that are produced in response to lipopolysaccharides (LPS, also called endotoxins), which are components of the cell wall of Gram-negative bacteria. Despite years of research, no drug has been developed that specifically targets the aggressive immune response that characterizes sepsis. Sepsis treatment mainly focuses on treating the symptoms of sepsis by securing the airway, correcting hypoxemia, and administering fluids. While antibiotics can eradicate the bacterial infection, they do not necessarily eliminate lipopolysaccharides, which are still capable of inducing a severe immune response when detached from the bacterium and after the infection has been cleared. Therefore, effective sepsis treatment options are still lacking. As such, novel treatments options directed at LPS sequestration and the inflammatory response to LPS are required.

About 1.6 million people are treated in U.S. hospitals annually for sepsis, 750,000 of these for severe sepsis. The mortality rate for sepsis in the US is between 23% and 43%. Sepsis was the 11th leading cause of death in 2010, and the leading cause of death in non-cardiac intensive care units. In developing countries, sepsis accounts for 60-80% of all deaths. In 2008, $14.6 billion were spent on hospitalizations for sepsis in the US.

SUMMARY OF INVENTION

In some aspects the invention is a method for decreasing the severity of an endotoxin mediated immune response, by contacting an immune cell that has been exposed to an endotoxin with a HDL nanoparticle (HDL-NP), wherein the HDL-NP has a zeta potential of less than −30 mV, wherein the HDL-NP comprises a core surrounded by a lipid layer shell and an apolipoprotein, and wherein the lipid layer includes at least one molecule of cardiolipin, phosphatidylethanolamine (PE), Dipalmitoylphosphatidylcholine (DPPC), and phosphatidylglycerol (PG), in an effective amount to decrease the severity of an endotoxin mediated immune response relative to an endotoxin mediated immune response in the absence of the HDL-NP.

In other aspects the invention is a method for treating sepsis, by administering to a subject having sepsis a HDL nanoparticle (HDL-NP), wherein the HDL-NP is less than 30 nm in diameter and comprises a core surrounded by a lipid layer shell and an apolipoprotein, and wherein the lipid layer shell includes at least one molecule of cardiolipin, phosphatidylethanolamine (PE), Dipalmitoylphosphatidylcholine (DPPC), and phosphatidylglycerol (PG), in an effective amount to treat sepsis.

In other aspects the invention is a method for treating sepsis by administering to a subject having sepsis a HDL nanoparticle (HDL-NP), wherein the HDL-NP comprises a core surrounded by a shell which is a lipid layer and an apolipoprotein, and wherein the HDL-NP is administered in a HDL sub-therapeutic dose effective to treat sepsis.

In other aspects the invention is a composition of a HDL nanoparticle (HDL-NP), wherein the HDL-NP is less than 30 nm in diameter and comprises a core surrounded by a lipid layer shell and an apolipoprotein, and wherein the lipid layer includes at least one molecule of cardiolipin, phosphatidylethanolamine (PE), Dipalmitoylphosphatidylcholine (DPPC), and phosphatidylglycerol (PG) and wherein the HDL-NP has a zeta potential of −40 mV-100 mV.

A method of contacting a cell in culture or an isolated biological sample that is contaminated with endotoxin with a composition as described herein in order to alter the response of the cell to the endotoxin is provided in other aspects.

The shell may have an inner surface and an outer surface wherein, optionally, a protein is bound to at least the outer surface of the shell. The protein may be a therapeutic agent. In some embodiments at least 80% of the lipids in the outer surface of the shell PG or cardiolipin. In other embodiments at least 95% of the lipids in the outer surface of the shell PG or cardiolipin. In yet other embodiments the lipids in the outer surface of the shell are comprised of 18:2 PG.

The lipid layer in some embodiments comprises phospholipids, unsaturated lipids, saturated lipids, and/or therapeutic lipids.

In other embodiments the core comprises an inorganic material. The inorganic material may be gold.

In other embodiments the HDL-NP is 10-30 nm in diameter, 15-30 nm in diameter or 15-20 nm in diameter.

The lipid layer may be a lipid bilayer or a lipid monolayer in embodiments. In some embodiments the lipid bilayer has an outer lipid layer that includes both cardiolipin and PG. In other embodiments the lipid bilayer has an inner layer that includes PE. In yet other embodiments the lipid bilayer has an outer lipid layer that includes only cardiolipin and PG and an inner layer that includes only PE. In yet other embodiments the lipid bilayer has an outer lipid layer that includes PG and an inner lipid layer that includes PE or the lipid bilayer has an outer lipid layer that includes only PG and an inner lipid layer that includes only PE. The lipid bilayer in other embodiments has an outer lipid layer that includes DPPC and an inner lipid layer that includes PE. In some embodiments the lipid bilayer has an outer lipid layer that includes only DPPC and an inner lipid layer that includes only PE. The term includes only when used in this context refers to the type of lipid in the lipid layer. The lipid layer may include other components such as proteins, but it only includes the specified lipid(s).

In some embodiments the HDL-NP has a zeta potential of less than −30 mV. In other embodiments the HDL-NP has a zeta potential of −40 mV-100 mV. In yet other embodiments the HDL-NP has a zeta potential of −60 mV-100 mV. In other embodiments the HDL-NP has a zeta potential of −65 mV-80 mV. In other embodiments the HDL-NP has a zeta potential of −70 mV-75 mV.

In some embodiments a therapeutic agent is bound to at least the outer surface of the shell. In other embodiments the therapeutic agent is a therapeutic sepsis agent. The therapeutic sepsis agent may be an antibiotic.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1A shows an absorbance spectrum for HDL NP containing cardiolipin and 18:2 PG as outer lipids (#4 in Table 1). Disperse nanoparticles exhibit a characteristic SPB in the ultraviolet-visible (UV/vis) spectrum around 520 nm and appear red in color, which is the case here. On the other hand, aggregated gold nanoparticles would appear purple and exhibit a red-shifted surface plasmon band. FIG. 1B shows that HDL NP bind lipopolysaccharides that are labeled with the fluorophor FITC (fluorescein isothiocyanate). Binding of HDL NP to LPS leads to quenching of the fluorescence of the attached FITC due to the close proximity of the fluorophor to the nanoparticle gold core.

FIG. 2A shows THP1-XBlue™-MD2-CD14 cells, which express the reporter protein secreted embryonic alkaline phosphatase (SEAP) as a response to activation of NF-κB and AP-1, treated with increasing concentrations of LPS derived from different bacteria and incubated for 24 h at 37° C. Afterwards, activity of SEAP was assessed using a Quantiblue-based assay. FIG. 2B is adapted from Erridge, C., Bennett-Guerrero, E., & Poxton, I. R. (2002). Structure and function of lipopolysaccharides. Microbes and Infection/Institut Pasteur, 4(8), 837-51. FIG. 2B shows the structure of $E.\ coli$ lipid A and $P.\ aureginosa$ lipid A.

FIG. 10 shows THP1-XBlue™-MD2-CD14 and THP1 cells treated with 2 ng/ml (THP1-XBlue™-MD2-CD14) or 10 ng/ml (THP1) LPS derived from $E.\ coli$ O55:B5 and 10 nM of HDL NP construct number 4 (see Table 1), or just with LPS or just with HDL NP. Cells were incubated for 24 h after LPS addition at 37° C. Cytokine levels in the cell supernatant were analyzed using an enzyme-linked immunosorbent assay (ELISA).

DETAILED DESCRIPTION

Figure 1A:
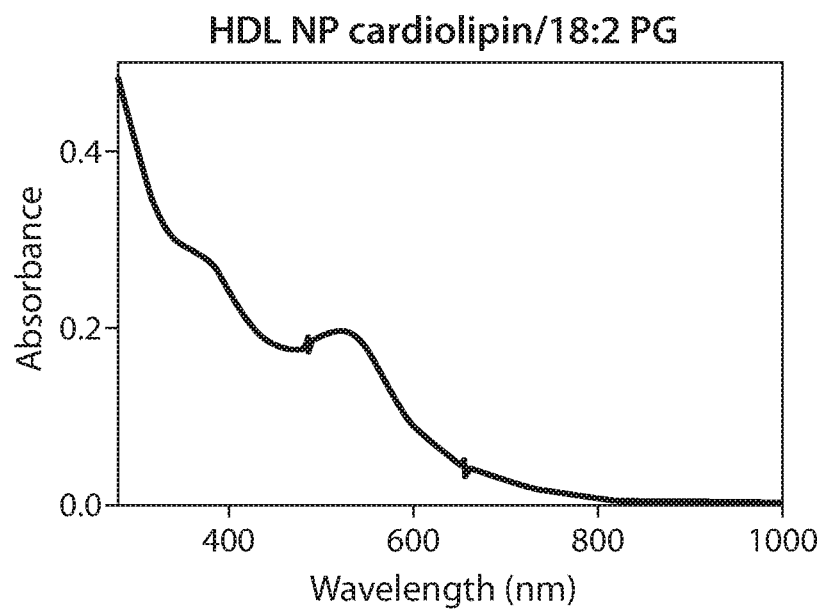
FIGS. 1A-1B.
Figure 1B:
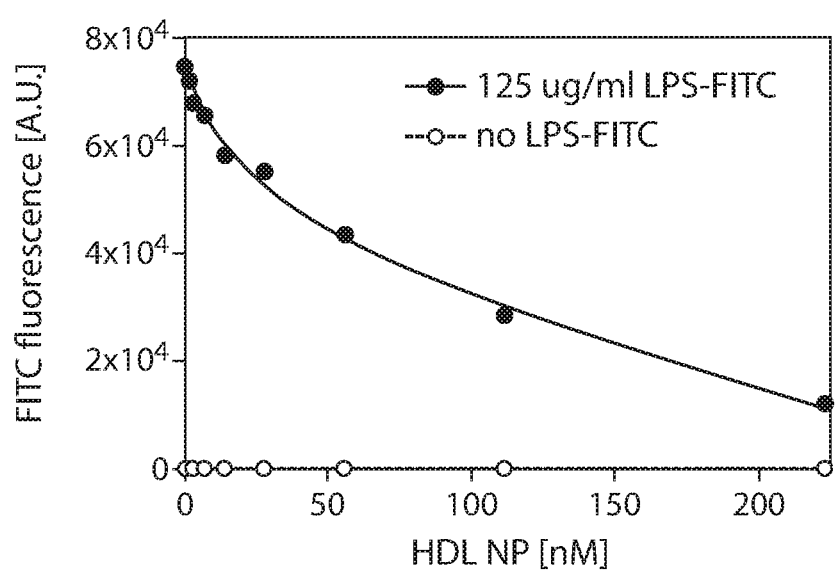

The invention described herein provides novel methods for treating sepsis, a disease with high mortality rates and very few treatment options. It was discovered, quite surprisingly, that HDL NP with certain physical-chemical properties have the ability to stably bind endotoxin such as bacterial lipopolysaccharide (LPS) and reduce an endotoxin induced immune response, much more efficiently than free human HDL. It was also discovered unexpectedly that low doses of HDL-NP, but not of human HDL, were capable of significantly reducing LPS-induced immune responses. Thus, low doses of HDL-NP, i.e. doses that would be sub-therapeutic for HDL alone, can be used to treat sepsis.

Sepsis is a major infection-related cause of death globally, leading to an estimated 8.5% of deaths (5 million) annually [Angus D, et al. Critical Care Medicine 2001; 29(7): 1303-

10; Kumar G, Kumar N, Taneja A, et al. Chest 201 1; 140: 1223-31]. Despite advances in modern medicine including new antibiotics and vaccines, early recognition and best practice treatments, and efficient well-equipped intensive care units [Angus D et al], the high rate of mortality, ~30%, has remained little changed for decades [Daniels R. J Antimicrobial Chemotherapy 201 1; 66(Suppl 2): ii1 1-ii23]. Sepsis affects more than 750,000 patients annually in the United States and has a mortality rate of from 30 to 65%, making it the tenth most common cause of death in the U.S. The risk of sepsis is found to be inversely related to age. Sepsis accounts for 60 to 80% of childhood deaths in the developing world. Due to its prevalence, hospital visits for sepsis or septicemia increased from 621,000 in the year 2000 to 1,141,000 in 2008. Mortality from sepsis is rising due to drug-resistant organisms, a growing elderly population, and increased incidence of immunosuppression. In economic terms, total costs for treating sepsis increased by an average of 11.9% each year between 1997 and 2008, adjusted for inflation, and amounted to $14.6 billion in the U.S. in 2008 and currently exceeding $17 billion. In addition to other hospital treatments, over 2.5 million patients are admitted annually to intensive care units (ICUs) for sepsis with the costs per individual ICU case adding $5,000 or more per day to total hospital costs and with treatment lasting at least two days and often more than 20 days. Sepsis is the most frequent cause of mortality in hospitalized patients. Nearly 50% of diagnosed sepsis cases in the U.S. are attributable to hospital-acquired infections (HAIs), which impose a major direct cost on hospitals due to little to no reimbursement from health insurers.

Sepsis, in general, can be described as the body's response to infection. This response is characterized by signs of inflammation that include, for example, vasodilation, leukocyte accumulation, and increased microvascular permeability, occurring in tissues that are remote from the infection. Sepsis is used to describe immune responses within a continuum ranging from infection to multiple organ dysfunction syndrome (MODS).

Systemic inflammatory response syndrome (SIRS) is defined as the presence of two or more of abnormal body temperature, heart rate, respiratory rate or blood gas, and white blood cell count, and sepsis is defined as SIRS in response to an infectious process. A systemic inflammatory response leading to a diagnosis of SIRS may be related to both infection and to numerous non-infective etiologies, including burns, pancreatitis, trauma, heat stroke, and neoplasia. While conceptually it may be relatively simple to distinguish between sepsis and non-septic SIRS, no diagnostic tools have been described to unambiguously distinguish these related conditions (Llewelyn and Cohen, Int. Care Med. 27: S10-S32, 2001). Severe sepsis is defined as sepsis with sepsis-induced organ dysfunction or tissue hypoperfusion (e.g., manifesting as hypotension, elevated lactate, or decreased urine output). Severe sepsis occurs when a natural immune response to an infection triggers widespread inflammation and blood clotting in tiny vessels throughout the body, which also involves failure of critical organs in the body and can thus lead to death. Finally, septic shock is severe sepsis plus persistently low blood pressure.

Current measures for diagnosing sepsis and estimating its severity, prognosis, and the efficacy of therapy include laboratory tests that monitor the evidence of infection; clotting problems; liver or kidney function; oxygen availability; electrolyte levels; and/or cardiovascular, neurologic, or hematologic function. Often these parameters are used to derive illness severity and/or prognosis scores like the Sequential Organ Failure Assessment (SOFA) score. Additionally, since more than 90% of sepsis cases involve bacterial infection, the "gold standard" for confirming infection has been microbial growth from blood, urine, pleural fluid, cerebrospinal fluid, peritoneal fluid, synnovial fluid, sputum, or other tissue specimens (Jaimes et al., Int. Care Med 29: 1368-71, published electronically Jun. 26, 2003). Blood tests may be done to check for infection, low blood oxygen level, abnormal acid-base balance, or poor organ function or organ failure; a chest x-ray or CT scan may be used to detect pneumonia or pulmonary edema or pneumatosis intestinalis; and/or a urine sample may be taken to detect infection. Blood cultures, may not become positive for several days after the blood has been taken, or for several days after the shock has developed. (Vincent, "Septic Shock." In: Fink et al, eds. Textbook of Critical Care. 5th ed. Philadelphia, Pa.: Saunders Elsevier; 2005: chap 147; Jones and Kline, "Shock." In: Marx, ed. Rosen's Emergency Medicine: Concepts and Clinical Practice. 6th ed. Philadelphia, Pa.: Mosby Elsevier; 2006: chap 4; Munford. "Severe sepsis and septic shock." In: Fauci and Harrison, eds. Harrison's Principles of Internal Medicine. 17th ed. New York, N.Y.: McGraw Hill; 2008:chap 265).

Bacterial endotoxins (including lipopolysaccharide, LPS) are potent inducers of inflammation and have been suggested as triggers for sepsis, as the cause of an early life-threatening cytokine storm and septic shock (Opal S M. Contributions to Nephrology 2010; 167: 14-24; Salomao R, et al. Shock 2012; 38:227-42). Experimental models of gram negative sepsis based on administration of bacterial endotoxin LPS have led to an improved understanding of the pathogenic mechanisms of lethal sepsis and conditions related to sepsis by activation of a common underlying inflammatory cytokine cascade. This cascade of host-response mediators include tumor necrosis factor (TNF), interleukin (IL)-1, platelet-activating factor (PAF) and other macrophage-derived factors that have been widely studied as acute, early mediators of eventual lethality in severe endotoxemia (Zhang and Tracey, in The Cytokine Handbook, 3rd ed. Ed. Thompson (Academic Press Limited, USA). 515-547, 1998).

Since all patients are different and the causes of sepsis are many, not every available treatment is right for each patient. Nevertheless, patients with severe sepsis or septic shock have a mortality rate of about 40-60%, with the elderly having the highest death rates (C. R. Wira, K. Dodge, J. Sather, J. Dziura, West J. Emerg. Med, 2014, 15(1), 51-59). A 2006 study showed that the risk of death from sepsis increases by 7.6% with every hour that passes before treatment begins (Kumar A., Roberts D., Wood K. E., Light B., Parrillo J. E., Sharma S., Suppes R, Feinstein D., Zanotti S., Taiberg L., Gurka D., Kumar A., Cheang M., Crit. Care Med., 2006, 34(6), 1589-96). Septic shock is the presence of infection associated with a systemic inflammatory response that results in physiologic alterations at the capillary endothelial level, manifesting as a drop in blood pressure. Septic shock can be caused by any type of bacteria, as well as some fungi and viruses. Most common in the elderly and very young children and infants, septic shock also occurs in people who suffer other illnesses, including diabetes, immune system disorders such as AIDS, diseases of the genitourinary, biliary, or intestinal tracts, cardiovascular disease (e.g. mesenterial infarction), leukemia, or lymphoma, or who have indwelling long-term catheters, recent surgeries, or use of steroids or antibiotics. Outward symptoms of septic shock include, e.g., reduced urine output (e.g., oliguria or anuria), cool, pale extremities; high or very low temperature, chills; lightheadedness; low blood pressure; low or absent urine output; palpitations; rapid heart rate; restlessness, agitation, lethargy, or confusion; shortness of breath; and skin rash or discoloration. However, these typical signs and symptoms are seen in advanced stages of septic shock.

Given that in the absence of an obvious infection, an absolute diagnosis of sepsis, severe sepsis, or septic shock (i.e., a diagnosis confirmed by the presence of pathogens in a blood or urine culture) can thus be delayed by several days, and that other conditions—such as traumatic shock and SIRS in the absence of infection—present with the same clinical symptoms, the present methods allow for the rapid and early diagnosis of sepsis, severe sepsis, septic shock in these subjects who can then be treated promptly with antibiotic or antimicrobial therapy. SIRS can be diagnosed in the presence of two or more of the following conditions: Temperature >38° C. or <36° C.; Heart rate >90 beats/min; Respiratory rate >20 breaths/min or PaCC <32 mm Hg; White blood cell count >12,000 cells/µt., <4000 cells/µt. (e.g., Levy et al, Crit Care Med 31: 1250-1256). Typically, sepsis is defined by the same criteria as SIRS, plus the presence of a documented infection or a suspected infection (a pathological process induced by a micro-organism) plus some of the following: general parameters (Fever (core temperature >38.3° C.), Hypothermia (core temperature <36° C., Heart rate >90 bpm or >2 SD above the normal value for age, Tachypnea: >30 bpm, Altered mental status, Significant edema or positive fluid balance (>20 ml/kg over 24 h), and/or Hyperglycemia (plasma glucose >110 mg/dl or 7.7 mM/l) in the absence of diabetes); Inflammatory parameters (Leukocytosis (white blood cell count >12,000/µl), Leukopenia (white blood cell count <4,000/µl), Normal white blood cell count with >10% immature forms, Plasma C reactive protein >2 SD above the normal value, and/or Plasma procalcitonin >2 SD above the normal value); Hemodynamic parameters (Arterial hypotension (systolic blood pressure <90 mmHg, mean arterial pressure <70, or a systolic blood pressure decrease >40 mmHg in adults or <2 SD below normal for age), Mixed venous oxygen saturation >70%, Cardiac index >3.5 1 min-1 m-2, Organ dysfunction parameters, Arterial hypoxemia (PaO2/FIO2<300), Acute oliguria (urine output <0.5 ml kg-1 h-1 or 45 mM/l for at least 2 h), Creatinine increase #0.5 mg/dl, Coagulation abnormalities (international normalized ratio >1.5 or activated partial thromboplastin time >60 s), Ileus (absent bowel sounds), Thrombocytopenia (platelet count <100,000/µl) and/or Hyperbilirubinemia (plasma total bilirubin >4 mg/dl or 70 mmol/l); and/or Tissue perfusion parameters (Hyperlactatemia (>3 mmol/l) and/or Decreased capillary refill or mottling) (Levy et al, Crit Care Med (2003) 31: 1250-1256; Levy et al, Intensive Care Med (2003) 29:530-538).

Clinical parameters that would be included to define patients with sepsis, severe sepsis and septic shock are leukocyte levels (and % of immature circulating leukocytes), temperature, heart rate, blood pressure, breathing, PaCC (SIRS criteria), the necessity for vasoconstrictors (e.g., norepinephrine), mean arterial pressure, oxygenation (FlO2) and systemic central venous oxygenation (ScVCh), mechanical ventilation, hourly urine production, and septic organ failure (ARDS=acute respiratory distress syndrome, ARF=acute renal failure, ALF=acute liver failure).

The subject diagnosed with sepsis may be hospitalised. The subject may be in intensive care. Subjects that may be at risk of acquiring sepsis may be selected from, but not limited, elderly subjects, surgical subjects, burns subjects, trauma subjects, cancer subjects, immunocompromised subjects (e.g. AIDS), subjects with acute respiratory distress syndrome (ARDS) or subjects with a hospital-acquired secondary (nosocomial) infection. The subject may have acquired sepsis through any means, for example, a bacterial infection, (either Gram-negative or Gram-positive) or by other pathogens such as fungi, viruses, and parasites and non-infective small stimuli such as superantigens. In one example, the subject does not have fungal sepsis. In a further example, the subject has a gram positive bacterial infection. In another example, the subject has a gram negative bacterial infection.

A diagnosis of sepsis in a subject may proceed according to criteria known in the art. One or more of the following may be symptomatic of a subject with sepsis, including presence of acute inflammation present throughout the entire body, frequently associated with fever and elevated white blood cell count (leucocytosis) or low white blood cell count and lower than average temperature, and vomiting. The subject may also be exhibiting one or more symptoms resulting from the host's immune response to the infection resulting in hemodynamic consequences and damage to organs. This host response has been termed SIRS and is characterised by an elevated heart rate (above 90 beats per minute), high respiratory rate (above 20 breaths per minute or a partial pressure of carbon dioxide in the blood of less than 32), abnormal white blood cell count (above 12,000 cells/mm3, lower than 4,000 cells/mm3, or greater than 10% band forms (immature white blood cells)) and elevated or lowered body temperature i.e. under 36° C. or over 38° C. Sepsis can be differentiated by SIRS by the presence of a known or suspected pathogen. For example, SIRS and a positive blood culture for a pathogen indicates the presence of sepsis. However, in many cases of sepsis no specific pathogen is identified.

The term "sepsis" will be understood as encompassing all the various forms of sepsis, for example, as derived according to the American College of Chest Physicians and the Society of Critical Care Medicine. Accordingly, the subject according to the present disclosure may be diagnosed as having SIRS, sepsis, severe sepsis or septic shock.

The subject may be diagnosed as having end-organ dysfunction, examples of which include lungs (acute lung injury or acute respiratory distress syndrome); brain (encephalopathy, ischemia, haemorrhage, microthrombi, mictoabscesses, multifocal necrotizing leukoencephalopathy); liver (disruption of protein synthetic function or disruption of metabolic function); kidney (oliguria and anuria, electrolyte abnormalities, volume overload); heart (systolic and diastolic failure, cellular damage); cardiovascular dysfunction (after fluid resuscitation with at least 40 ml/kg of crystalloid; hypotentsion, vasopressor requirement, acidosis, oliguria, core to peripheral temperature difference >3 SC); respiratory dysfunction (in the absence of cyanotic heart disease or known chronic lung disease); neurologic dysfunction; hematologic dysfunction (platelet count <80,000/mm3 or 50% drop from maximum in chronically thrombocytopenic patients; disseminated intravascular coagulation); renal dysfunction; or hepatic dysfunction. With the proviso that the subject is lymphopenic, any of the above forms of sepsis may be treated according to the methods of the present disclosure.

The HDL-NP of the invention may be delivered with other therapeutic agents. For treating sepsis. The HDL-NP may be co-administered with the therapeutic agent. For instance the HDL-NP may be delivered together with or separately from the therapeutic agent at the same time or different times. Alternatively the therapeutic agent may be linked to the HDL-NP. For instance it may be linked to the outer or inner surface of the lipid layer shell or it may be linked to or included within the core. A therapeutic agent for treating sepsis is any known therapeutic agent, such as antibiotics corticosteroids or vasopressors.

Antibiotics are used to treat infection and sepsis. Examples of antibiotics that could be used to treat sepsis include, but are not limited to imipenem/cilastatin, meropenem, piperacillin and tazobactam, ampicillin and sulbactam, clindamycin, metronidazole, cefepime, levofloxacin, vancomycin, imethoprim/sulfamethoxazole, aztreonam, linezolid, ceftriaxone, daptomycin, nafcillin, rifampin, daptomycin, tigecycline, cefotaxime, ticarcillin-clavulanate, ciprofloxacin. The antibiotics can be combined with fluids for treatment of sepsis. While there are several types of fluids that can be administered intravenously, some are standard in treating sepsis. Crystalloid fluids and colloids are examples of fluids used for treatment. Examples of crystalloid fluids include, but are not limited to normal saline (0.9% NaCl), lactated ringer, and plasmalyte. Examples of colloids include, but are not limited to albumin and dextran.

Corticosteroids and vassopressors may also be used to treat sepsis. Examples of corticosteroids include, but are not limited to hydrocortisone and dexamethasone. Examples of vasopressors include, but are not limited to norepinephrine, dopamine, dobutamine, epinephrine, phenylephrine, and vasopressin.

The examples described above are non-limiting examples and can be used in any combination. The above mentioned classes and non-limiting examples of treatments can also be used in combination with HDL NPs disclosed herein.

A HDL sub-therapeutic dose, as used herein refers to a dose that would not normally result in a therapeutic response for free or recombinant HDL. The dose of HDL NP useful at this dose would be a molar equivalent or less of the free HDL. In other embodiments the dose of HDL NP useful at this dose would be based upon a lower amount (g/mL or g/kg) of apoA1 protein in the HDL NP versus any other recombinant HDL. An equimolar concentration of HDL-NP and human HDL is a concentration in which the apolipoprotein content of both species is equivalent.

The HDL-NP of the invention may have a zeta potential of less than −30mV and in some embodiments may be −30 to −100 mV. Zeta potential is a measure of the magnitude of the electrostatic or charge repulsion/attraction between particles, and is one of the fundamental parameters known to affect stability. The electric potential at the boundary of the outer layer of the HDL-NP and the surface of a surrounding particle or solution is known as the Zeta potential of the particles. Nanoparticles with a zeta potential between −10 and +10 mV are considered approximately neutral, while nanoparticles with zeta potentials of greater than +30 mV or less than −30 mV are considered strongly cationic and strongly anionic, respectively. In some embodiments the zeta potential of the HDL-NP are within one of the following ranges: −30 to −100, −40 to −100, −50 to −100, −60 to −100, −70 to −100, −80 to −100, −90 to −100, −40 to −90, 50 to −90, −60 to −90, −70 to −90, −80 to −90, 50 to −80, −60 to −80, −70 to −80, −40 to −80, 50 to −70, −60 to −70, −70 to −75, or −65 to −75, The HDL-NP useful in the methods of the invention is a nanostructure composed of a core, which may be an inorganic material, surrounded by a shell of a lipid layer. The nanostructure also includes a protein such as an apolipoprotein.

The shell may have an inner surface (facing the core) and an outer surface (facing the surroundings), such that the apolipoprotein may be adsorbed on the outer shell and/or incorporated between the inner surface and outer surface of the shell. The shell is comprised of lipids and may be a lipid monolayer or bilayer, for instance.

It should be understood that a shell which surrounds a core need not completely surround the core, although such embodiments may be possible. For example, the shell may surround at least 50%, at least 60%, at least 70%, at least 80%, at least 90%, or at least 99% of the surface area of a core. In some cases, the shell substantially surrounds a core. In other cases, the shell completely (100%) surrounds a core. The components of the shell may be distributed evenly across a surface of the core in some cases, and unevenly in other cases. For example, the shell may include portions (e.g., holes) that do not include any material in some cases. If desired, the shell may be designed to allow penetration and/or transport of certain molecules and components into or out of the shell, but may prevent penetration and/or transport of other molecules and components into or out of the shell. The ability of certain molecules to penetrate and/or be transported into and/or across a shell may depend on, for example, the packing density of the components forming the shell and the chemical and physical properties of the components forming the shell. The shell may include one layer of material, or multilayers of materials in some embodiments.

Optionally, components of the particle can be crosslinked to one another. Crosslinking of components of a shell can, for example, allow the control of transport of species into the shell, or between an area exterior to the shell and an area interior of the shell. For example, relatively high amounts of crosslinking may allow certain small, but not large, molecules to pass into or through the shell, whereas relatively low or no crosslinking can allow larger molecules to pass into or through the shell. Additionally, the components forming the shell may be in the form of a monolayer or a multilayer, which can also facilitate or impede the transport or sequestering of molecules. In one exemplary embodiment, shell includes a lipid bilayer that is arranged to sequester cholesterol and/or control cholesterol efflux out of cells.

The core of the nanostructure whether being a solid core or a hollow core, may have any suitable shape and/or size. For instance, the core may be substantially spherical, non-spherical, oval, rod-shaped, pyramidal, cube-like, disk-shaped, wire-like, or irregularly shaped. The core (e.g., a nanostructure core or a hollow core) may have a largest cross-sectional dimension (or, sometimes, a smallest cross-section dimension) of, for example, less than or equal to about 500 nm, less than or equal to about 250 nm, less than or equal to about 100 nm, less than or equal to about 75 nm, less than or equal to about 50 nm, less than or equal to about 40 nm, less than or equal to about 35 nm, less than or equal to about 30 nm, less than or equal to about 25 nm, less than or equal to about 20 nm, less than or equal to about 15 nm, or less than or equal to about 5 nm. In some cases, the core has an aspect ratio of greater than about 1:1, greater than 3:1, or greater than 5:1. As used herein, "aspect ratio" refers to the ratio of a length to a width, where length and width measured perpendicular to one another, and the length refers to the longest linearly measured dimension.

The core may be formed of an inorganic material. The inorganic material may include, for example, a metal (e.g., Ag, Au, Pt, Fe, Cr, Co, Ni, Cu, Zn, and other transition metals), a semiconductor (e.g., silicon, silicon compounds and alloys, cadmium selenide, cadmium sulfide, indium arsenide, and indium phosphide), or an insulator (e.g., ceramics such as silicon oxide). The inorganic material may be present in the core in any suitable amount, e.g., at least 1 wt %, 5 wt %, 10 wt %, 25 wt %, 50 wt %, 75 wt %, 90 wt %, or 99 wt %. In one embodiment, the core is formed of 100 wt % inorganic material. The core may, in some cases, be in the form of a quantum dot, a carbon nanotube, a carbon nanowire, or a carbon nanorod. In some cases, the core comprises, or is formed of, a material that is not of biological origin. In some embodiments, a nanostructure includes or may be formed of one or more organic materials such as a synthetic polymer and/or a natural polymer. Examples of synthetic polymers include non-degradable polymers such as polymethacrylate and degradable polymers such as polylactic acid, polyglycolic acid and copolymers thereof. Examples of natural polymers include hyaluronic acid, chitosan, and collagen.

Furthermore, a shell of a structure can have any suitable thickness. For example, the thickness of a shell may be at least 10 Angstroms, at least 0.1 nm, at least 1 nm, at least 2 nm, at least 5 nm, at least 7 nm, at least 10 nm, at least 15 nm, at least 20 nm, at least 30 nm, at least 50 nm, at least 100 nm, or at least 200 nm (e.g., from the inner surface to the outer surface of the shell). In some cases, the thickness of a shell is less than 200 nm, less than 100 nm, less than 50 nm, less than 30 nm, less than 20 nm, less than 15 nm, less than 10 nm, less than 7 nm, less than 5 nm, less than 3 nm, less than 2 nm, or less than 1 nm (e.g., from the inner surface to the outer surface of the shell). Such thicknesses may be determined prior to or after sequestration of molecules as described herein.

The shell of a structure described herein may comprise any suitable material, such as a hydrophobic material, a hydrophilic material, and/or an amphiphilic material. Although the shell may include one or more inorganic materials such as those listed above for the nanostructure core, in many embodiments the shell includes an organic material such as a lipid or certain polymers. The components of the shell may be chosen, in some embodiments, to facilitate the binding capacity.

In one set of embodiments, a structure described herein or a portion thereof, such as a shell of a structure, includes one or more natural or synthetic lipids or lipid analogs (i.e., lipophilic molecules). One or more lipids and/or lipid analogues may form a single layer or a multi-layer (e.g., a bilayer) of a structure. In some instances where multi-layers are formed, the natural or synthetic lipids or lipid analogs interdigitate (e.g., between different layers). Non-limiting examples of natural or synthetic lipids or lipid analogs include fatty acyls, glycerolipids, glycerophospholipids, sphingolipids, saccharolipids and polyketides (derived from condensation of ketoacyl subunits), and sterol lipids and prenol lipids (derived from condensation of isoprene subunits).

In one particular set of embodiments, a structure described herein includes one or more phospholipids. The one or more phospholipids may include, for example, phosphatidylcholine, phosphatidylglycerol, lecithin, β, γ-dipalmitoyl-α-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, 1,2-dipalmitoyl-sn-glycero-3-phosphothioethanol, and combinations thereof. In some cases, a shell (e.g., a bilayer) of a structure includes 50-200 natural or synthetic lipids or lipid analogs (e.g., phospholipids). For example, the shell may include less than about 500, less than about 400, less than about 300, less than about 200, or less than about 100 natural or synthetic lipids or lipid analogs (e.g., phospholipids), e.g., depending on the size of the structure.

Non-phosphorus containing lipids may also be used such as stearylamine, docecylamine, acetyl palmitate, and fatty acid amides. In other embodiments, other lipids such as fats, oils, waxes, cholesterol, sterols, fat-soluble vitamins (e.g., vitamins A, D, E and K), glycerides (e.g., monoglycerides, diglycerides, triglycerides) can be used to form portions of a structure described herein.

A portion of a structure described herein such as a shell or a surface of a nanostructure may optionally include one or more alkyl groups, e.g., an alkane-, alkene-, or alkyne-containing species, that optionally imparts hydrophobicity to the structure. An "alkyl" group refers to a saturated aliphatic group, including a straight-chain alkyl group, branched-chain alkyl group, cycloalkyl (alicyclic) group, alkyl substituted cycloalkyl group, and cycloalkyl substituted alkyl group. The alkyl group may have various carbon numbers, e.g., between C2 and C40, and in some embodiments may be greater than C5, C10, C15, C20, C25, C30, or C35. In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., C1-C12 for straight chain, C3-C12 for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclohexyl, and the like.

The alkyl group may include any suitable end group, e.g., a thiol group, an amino group (e.g., an unsubstituted or substituted amine), an amide group, an imine group, a carboxyl group, or a sulfate group, which may, for example, allow attachment of a ligand to a nanostructure core directly or via a linker. For example, where inert metals are used to form a nanostructure core, the alkyl species may include a thiol group to form a metal-thiol bond. In some instances, the alkyl species includes at least a second end group. For example, the species may be bound to a hydrophilic moiety such as polyethylene glycol. In other embodiments, the second end group may be a reactive group that can covalently attach to another functional group. In some instances, the second end group can participate in a ligand/receptor interaction (e.g., biotin/streptavidin).

In some embodiments, the shell includes a polymer. For example, an amphiphilic polymer may be used. The polymer may be a diblock copolymer, a triblock copolymer, etc., e.g., where one block is a hydrophobic polymer and another block is a hydrophilic polymer. For example, the polymer may be a copolymer of an α-hydroxy acid (e.g., lactic acid) and polyethylene glycol. In some cases, a shell includes a hydrophobic polymer, such as polymers that may include certain acrylics, amides and imides, carbonates, dienes, esters, ethers, fluorocarbons, olefins, sytrenes, vinyl acetals, vinyl and vinylidene chlorides, vinyl esters, vinyl ethers and ketones, and vinylpyridine and vinylpyrrolidones polymers. In other cases, a shell includes a hydrophilic polymer, such as polymers including certain acrylics, amines, ethers, styrenes, vinyl acids, and vinyl alcohols. The polymer may be charged or uncharged. As noted herein, the particular components of the shell can be chosen so as to impart certain functionality to the structures.

Where a shell includes an amphiphilic material, the material can be arranged in any suitable manner with respect to the nanostructure core and/or with each other. For instance, the amphiphilic material may include a hydrophilic group that points towards the core and a hydrophobic group that extends away from the core, or, the amphiphilic material may include a hydrophobic group that points towards the core and a hydrophilic group that extends away from the core. Bilayers of each configuration can also be formed.

The structures described herein may also include one or more proteins, polypeptides and/or peptides (e.g., synthetic peptides, amphiphilic peptides). In one set of embodiments, the structures include proteins, polypeptides and/or peptides that can increase the rate of cholesterol transfer or the cholesterol-carrying capacity of the structures. The one or more proteins or peptides may be associated with the core (e.g., a surface of the core or embedded in the core), the shell (e.g., an inner and/or outer surface of the shell, and/or embedded in the shell), or both. Associations may include covalent or non-covalent interactions (e.g., hydrophobic and/or hydrophilic interactions, electrostatic interactions, van der Waals interactions).

An example of a suitable protein that may associate with a structure described herein is an apolipoprotein, such as apolipoprotein A (e.g., apo A-I, apo A-II, apo A-IV, and apo A-V), apolipoprotein B (e.g., apo B48 and apo B100), apolipoprotein C (e.g., apo C-I, apo C-II, apo C-III, and apo C-IV), and apolipoproteins D, E, and H. Specifically, apo A1, apo A2, and apo E promote transfer of cholesterol and cholesteryl esters to the liver for metabolism and may be useful to include in structures described herein. Additionally or alternatively, a structure described herein may include one or more peptide analogues of an apolipoprotein, such as one described above. A structure may include any suitable number of, e.g., at least 1, 2, 3, 4, 5, 6, or 10, apolipoproteins or analogues thereof. In certain embodiments, a structure includes 1-6 apolipoproteins, similar to a naturally occurring HDL particle. Of course, other proteins (e.g., non-apolipoproteins) can also be included in structures described herein.

Optionally, one or more enzymes may also be associated with a structure described herein. For example, lecithin-cholesterol acyltransferase is an enzyme which converts free cholesterol into cholesteryl ester (a more hydrophobic form of cholesterol). In naturally-occurring lipoproteins (e.g., HDL and LDL), cholesteryl ester is sequestered into the core of the lipoprotein, and causes the lipoprotein to change from a disk shape to a spherical shape. Thus, structures described herein may include lecithin-cholesterol acyltransferase to mimic HDL and LDL structures. Other enzymes such as cholesteryl ester transfer protein (CETP) which transfers esterified cholesterol from HDL to LDL species may also be included.

Another example of a class of suitable proteins that may associate with a structure described herein are acute phase serum protein lipopolysaccharide binding protein (LBP), which naturally binds lipopolysaccharides, protein homologs or protein analogs of LBP, or peptides derived from LBP.

It should be understood that the components described herein, such as the lipids, phospholipids, alkyl groups, polymers, proteins, polypeptides, peptides, enzymes, bioactive agents, nucleic acids, and species for targeting described above (which may be optional), may be associated with a structure in any suitable manner and with any suitable portion of the structure, e.g., the core, the shell, or both. For example, one or more such components may be associated with a surface of a core, an interior of a core, an inner surface of a shell, an outer surface of a shell, and/or embedded in a shell.

Additionally, the components described herein, such as the lipids, phospholipids, alkyl groups, polymers, proteins, polypeptides, peptides, enzymes, bioactive agents, nucleic acids, and species for targeting described above, may be associated with a structure described herein prior to administration to a subject or biological sample and/or after administration to a subject or biological sample. For example, in some cases a structure described herein includes a core and a shell which is administered in vivo or in vitro, and the structure has a greater therapeutic effect after sequestering one or more components (e.g., an apolipoprotein) from a subject or biological sample. That is, the structure may use natural components from the subject or biological sample to increase efficacy of the structure after it has been administered.

A variety of methods can be used to fabricate the nanostructures described herein. Examples of methods are provided in International Patent Publication No. WO/2009/131704, filed Apr. 24, 2009 and entitled, "Nanostructures Suitable for Sequestering Cholesterol and Other Molecules", which is incorporated herein by reference in its entirety for all purposes.

The HDL-NP may be used in "pharmaceutical compositions" or "pharmaceutically acceptable" compositions, which comprise a therapeutically effective amount of one or more of the structures described herein, formulated together with one or more pharmaceutically acceptable carriers, additives, and/or diluents. The pharmaceutical compositions described herein may be useful for treating sepsis or other related diseases. It should be understood that any suitable structures described herein can be used in such pharmaceutical compositions, including those described in connection with the figures.

The pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those structures, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The structures described herein may be orally administered, parenterally administered, subcutaneously administered, and/or intravenously administered. In certain embodiments, a structure or pharmaceutical preparation is administered orally. In other embodiments, the structure or pharmaceutical preparation is administered intravenously. Alternative routes of administration include sublingual, intramuscular, and transdermal administrations.

Pharmaceutical compositions described herein include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, from about 5% to about 70%, or from about 10% to about 30%.

The inventive compositions suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a structure described herein as an active ingredient. The HDL-NP may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered structure is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the structures described herein include pharmaceutically acceptable emulsions, microemulsions, solutions, dispersions, suspensions, syrups and elixirs. In addition to the inventive structures, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions described herein (e.g., for rectal or vaginal administration) may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the body and release the structures.

Dosage forms for the topical or transdermal administration of a structure described herein include powders, sprays, ointments, pastes, foams, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to the inventive structures, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the structures described herein, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a structure described herein to the body. Dissolving or dispersing the structure in the proper medium can make such dosage forms. Absorption enhancers can also be used to increase the flux of the structure across the skin. Either providing a rate controlling membrane or dispersing the structure in a polymer matrix or gel can control the rate of such flux.

Ophthalmic formulations, eye ointments, powders, solutions and the like, are also contemplated as being within the scope of this invention.

Pharmaceutical compositions described herein suitable for parenteral administration comprise one or more inventive structures in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the inventive structures may be facilitated by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Delivery systems suitable for use with structures and compositions described herein include time-release, delayed release, sustained release, or controlled release delivery systems, as described herein. Such systems may avoid repeated administrations of the structures in many cases, increasing convenience to the subject and the physician. Many types of release delivery systems are available and known to those of ordinary skill in the art. They include, for example, polymer based systems such as polylactic and/or polyglycolic acid, polyanhydrides, and polycaprolactone; nonpolymer systems that are lipid-based including sterols such as cholesterol, cholesterol esters, and fatty acids or neutral fats such as mono-, di- and triglycerides; hydrogel release systems; silastic systems; peptide based systems; wax coatings; compressed tablets using conventional binders and excipients; or partially fused implants. Specific examples include, but are not limited to, erosional systems in which the composition is contained in a form within a matrix, or diffusional systems in which an active component controls the release rate. The compositions may be as, for example, microspheres, hydrogels, polymeric reservoirs, cholesterol matrices, or polymeric systems. In some embodiments, the system may allow sustained or controlled release of the active compound to occur, for example, through control of the diffusion or erosion/degradation rate of the formulation. In addition, a pump-based hardware delivery system may be used in some embodiments. The structures and compositions described herein can also be combined (e.g., contained) with delivery devices such as syringes, pads, patches, tubes, films, MEMS-based devices, and implantable devices.

Use of a long-term release implant may be particularly suitable in some cases. "Long-term release," as used herein, means that the implant is constructed and arranged to deliver therapeutic levels of the composition for at least about 30 or about 45 days, for at least about 60 or about 90 days, or even longer in some cases. Long-term release implants are well known to those of ordinary skill in the art, and include some of the release systems described above.

Injectable depot forms can be made by forming microencapsule matrices of the structures described herein in biodegradable polymers such as polylactide-polyglycolide. Depending on the ratio of structure to polymer, and the nature of the particular polymer employed, the rate of release of the structure can be controlled. Examples of other biodegradable polymers include poly(orthoesters) and poly(anhydrides).

When the structures described herein are administered as pharmaceuticals, to humans and animals, they can be given per se or as a pharmaceutical composition containing, for example, about 0.1% to about 99.5%, about 0.5% to about 90%, or the like, of structures in combination with a pharmaceutically acceptable carrier.

The administration may be localized (e.g., to a particular region, physiological system, tissue, organ, or cell type) or systemic, depending on the condition to be treated. For example, the composition may be administered through parental injection, implantation, orally, vaginally, rectally, buccally, pulmonary, topically, nasally, transdermally, surgical administration, or any other method of administration where access to the target by the composition is achieved. Examples of parental modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be useful for some treatments because of the convenience to the patient as well as the dosing schedule.

Regardless of the route of administration selected, the structures described herein, which may be used in a suitable hydrated form, and/or the inventive pharmaceutical compositions, are formulated into pharmaceutically-acceptable dosage forms by conventional methods known to those of skill in the art.

The compositions described herein may be given in dosages, e.g., at the maximum amount while avoiding or minimizing any potentially detrimental side effects. The compositions can be administered in effective amounts, alone or in a combinations with other compounds. For example, when treating cancer, a composition may include the structures described herein and a cocktail of other compounds that can be used to treat cancer. When treating conditions associated with abnormal lipid levels, a composition may include the structures described herein and other compounds that can be used to reduce lipid levels (e.g., cholesterol lowering agents).

The phrase "therapeutically effective amount" as used herein means that amount of a material or composition comprising an inventive structure which is effective for producing some desired therapeutic effect in a subject at a reasonable benefit/risk ratio applicable to any medical treatment. Accordingly, a therapeutically effective amount may, for example, prevent, minimize, or reverse disease progression associated with sepsis. Disease progression can be monitored by clinical observations, laboratory and imaging investigations apparent to a person skilled in the art. A therapeutically effective amount can be an amount that is effective in a single dose or an amount that is effective as part of a multi-dose therapy, for example an amount that is administered in two or more doses or an amount that is administered chronically.

The effective amount of any one or more structures described herein may be from about 10 ng/kg of body weight to about 1000 mg/kg of body weight, and the frequency of administration may range from once a day to once a month. However, other dosage amounts and frequencies also may be used as the invention is not limited in this respect. A subject may be administered one or more structure described herein in an amount effective to treat one or more diseases or bodily conditions described herein.

An effective amount may depend on the particular condition to be treated. The effective amounts will depend, of course, on factors such as the severity of the condition being treated; individual patient parameters including age, physical condition, size and weight; concurrent treatments; the frequency of treatment; or the mode of administration. These factors are well known to those of ordinary skill in the art and can be addressed with no more than routine experimentation. In some cases, a maximum dose be used, that is, the highest safe dose according to sound medical judgment.

Actual dosage levels of the active ingredients in the pharmaceutical compositions described herein may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular inventive structure employed, the route of administration, the time of administration, the rate of excretion or metabolism of the particular structure being employed, the duration of the treatment, other drugs, compounds and/or materials used in combination with the particular structure employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the structures described herein employed in the pharmaceutical composition at levels lower than that required to achieve the desired therapeutic effect and then gradually increasing the dosage until the desired effect is achieved.

In some embodiments, a structure or pharmaceutical composition described herein is provided to a subject chronically. Chronic treatments include any form of repeated administration for an extended period of time, such as repeated administrations for one or more months, between a month and a year, one or more years, or longer. In many embodiments, a chronic treatment involves administering a structure or pharmaceutical composition repeatedly over the life of the subject. For example, chronic treatments may involve regular administrations, for example one or more times a day, one or more times a week, or one or more times a month. In general, a suitable dose such as a daily dose of a structure described herein will be that amount of the structure that is the lowest dose effective to produce a therapeutic effect. Such an effective dose will generally depend upon the factors described above. Generally doses of the structures described herein for a patient, when used for the indicated effects, will range from about 0.0001 to about 100 mg per kg of body weight per day. The daily dosage may range from 0.001 to 50 mg of compound per kg of body weight, or from 0.01 to about 10 mg of compound per kg of body weight. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six or more sub-doses administered separately at appropriate intervals throughout the day, optionally, in unit dosage forms. For example, instructions and methods may include dosing regimens wherein specific doses of compositions, especially those including structures described herein having a particular size range, are administered at specific time intervals and specific doses to achieve reduction of cholesterol (or other lipids) and/or treatment of disease while reducing or avoiding adverse effects or unwanted effects.

While it is possible for a structure described herein to be administered alone, it may be administered as a pharmaceutical composition as described above. The present invention also provides any of the above-mentioned compositions useful for diagnosing, preventing, treating, or managing a disease or bodily condition packaged in kits, optionally including instructions for use of the composition. That is, the kit can include a description of use of the composition for participation in any disease or bodily condition, including those associated with abnormal lipid levels. The kits can further include a description of use of the compositions as discussed herein. The kit also can include instructions for use of a combination of two or more compositions described herein. Instructions also may be provided for administering the composition by any suitable technique, such as orally, intravenously, or via another known route of drug delivery.

The kits described herein may also contain one or more containers, which can contain components such as the structures, signaling entities, and/or biomolecules as described. The kits also may contain instructions for mixing, diluting, and/or administrating the compounds. The kits also can include other containers with one or more solvents, surfactants, preservatives, and/or diluents (e.g., normal saline (0.9% NaCl), or 5% dextrose) as well as containers for mixing, diluting or administering the components to the sample or to the patient in need of such treatment.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are used, the liquid form may be concentrated or ready to use. The solvent will depend on the particular inventive structure and the mode of use or administration. Suitable solvents for compositions are well known and are available in the literature.

The kit, in one set of embodiments, may comprise one or more containers such as vials, tubes, and the like, each of the containers comprising one of the separate elements to be used in the method. For example, one of the containers may comprise a positive control in the assay. Additionally, the kit may include containers for other components, for example, buffers useful in the assay.

As used herein, a "subject" or a "patient" refers to any mammal (e.g., a human), for example, a mammal that may be susceptible to a disease or bodily condition such as a disease or bodily condition associated with abnormal lipid levels. Examples of subjects or patients include a human, a non-human primate, a cow, a horse, a pig, a sheep, a goat, a dog, a cat or a rodent such as a mouse, a rat, a hamster, or a guinea pig. Generally, the invention is directed toward use with humans. A subject may be a subject diagnosed with a certain disease or bodily condition or otherwise known to have a disease or bodily condition such as sepsis. In some embodiments, a subject may be diagnosed as, or known to be, at risk of developing a disease or bodily condition.

In some embodiments, a subject may be diagnosed with, or otherwise known to have, a disease or bodily condition associated with sepsis or severe inflammation. Sepsis, or endotoxemia, as used interchangeably herein, refer to a systemic inflammatory response to an infection (e.g., bacterial, viral, fungal, or parasitic infection). Bacterial sepsis can be causes by both gram-positive and gram-negative bacteria, the latter primarily due to the bacterial endotoxin liposaccaride (LPS), and can be induced by a variety of bacteria, for example *Pseudomonas aeruginosa, Escherichia coli, Proteus, Klebsiella, Enterobacter* and *Serratia*. Sepsis also includes septic shock, and any disease or disorder related to resulting from septic shock, including, for example, hypotension, oliguria, tachycardia, tachypnea, and fever.

The signs and symptoms of severe sepsis may be subtle. Sepsis is considered a systemic inflammatory response syndrome (SIRS) resulting from infection (bacterial, viral, fungal, or parasitic), and is associated with a continuum of events which may include severe sepsis, septic shock, multiple organ dysfunction syndrome (MODS). SIRS typically includes, but is not limited to, the presence of more than one of the following manifestations: temperature $\geq 38°$ C. or $\leq 36°$ C. ($\geq 100.4°$ F. or $\leq 96.8°$ F.), Heart rate $\geq 90$ beats/min, Tachypnea, as manifested by a respiratory rate $\geq 20$ breaths/min or hyperventilation, as indicated by a $PaCO2 \leq 32$ mmHg, alteration of white blood cell count $\geq 12,000$ cells/mm3, $\leq 4,000$ cells/mm3, or the presence of $\geq 10\%$ immature neutrophils. Other clinical manifestation may indicative of SIRS and, therefore, sepsis in some cases. In some cases, sepsis is determined by detecting pathogens in a clinical sample (e.g., by culture, stain, or polymerase chain reaction (PCR)).

In some aspects the invention provides methods for the prophylactic treatment of sepsis in an individual. For example, the methods and compositions of the invention can be used to prevent sepsis in an individual at-risk of sepsis. There are a variety of situations known in the art in which an individual may be deemed at-risk of sepsis, for example, immunocompromised individuals, patients receiving cancer therapy, low birth weight infants, intra-abdominal surgery patients, individuals having severe urinary tract infection, intensive care unit patients receiving anti-infective agents, individuals having severe community-acquired pneumonia (CAP), burn and trauma victims, individuals having HIV/AIDS, Meningitis, or Cellulitis, hospitalized patients receiving cytotoxic and immunosuppressive agents and individuals having chronic diseases including diabetes, heart failure, chronic renal failure, and hepatitis. These examples are not meant to be limiting and the prophylactic treatment methods of the invention may be useful in any instance where an individual is at risk of sepsis.

In other aspects, the invention provides a method for treating sepsis in a subject that has sepsis by administering to the subject an HDL-NP. The methods may involve delivering a HDL-NP alone or in combination with other therapeutics. The other therapeutic may be, for instance, other agents known to aid in the treatment or prevention of sepsis, e.g., antibiotics, anti-TNF-α antibodies, and/or anti-LPS antibodies, which may be produced as described in U.S. Pat. No. 6,315,999, the contents of which are incorporated herein by reference).

The compositions of the invention are also useful for a variety of research purposes. For instance the compositions may be used to treat cells in culture or from a biological sample that are or potentially are endotoxin contaminated. For instance, a precious cell line i.e., isolated from patients, that is contaminated may be treated with the compositions of the invention in order to eradicate the infection and save the cell line or biological sample.

A "biological sample," as used herein, is any cell, body tissue, or body fluid sample obtained from a subject. Non-limiting examples of body fluids include, for example, lymph, saliva, blood, urine, and the like. Samples of tissue and/or cells for use in the various methods described herein can be obtained through standard methods including, but not limited to, tissue biopsy, including punch biopsy and cell scraping, needle biopsy; or collection of blood or other bodily fluids by aspiration or other suitable methods.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Equivalents

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

In order that the invention described herein may be more fully understood, the following examples are set forth. The examples described in this application are offered to illustrate the compounds, pharmaceutical compositions, and methods provided herein and are not to be construed in any way as limiting their scope.

EXAMPLES

Example 1

HDL NP Reduce LPS-Induced Immune Response in a Human Monocytic Cell Line

HDL Nanoparticle (NP) Synthesis: We synthesized HDL NP that are based on a 6 nm gold scaffold, covered by a covalently attached lipid bilayer, and stabilized by ApoA 1. Size, shape, cholesterol binding and efflux properties of the HDL NP have been shown to be comparable to the ones of natural HDL. Novel HDL NP have now been developed that have activity surprisingly beneficial in the inhibition of inflammatory mediators, that are, thus, useful in the treatment of bacterial sepsis. These particles are in the low nanometer range and stable, as indicated by absorbance, dynamic light scattering and zeta potential measurements. Importantly, our HDL NP bind to lipopolysaccharides in vitro. The HDL NP can be used for the detoxification of LPS during bacterial sepsis. Additionally, the data demonstrate that there are optimal conjugates that modify macrophage responses to LPS challenge.

TABLE 1

Different HDL NP constructs developed for the treatment of bacterial sepsis

| No | Gold particle size [nm] | Apo A1? | Inner Lipid | Inner Lipid Excess over gold | Outer Lipid I | Outer Lipid I Excess over gold | Outer Lipid II | Outer Lipid II Excess over gold | Name |
|---|---|---|---|---|---|---|---|---|---|
| 1 | 5 | + | PDP PE 16:0 | 250x | DPPC | 250x | | | HDL NP classic with Apo |
| 2 | 5 | − | PDP PE 16:0 | 250x | DPPC | 250x | | | HDL NP classic without Apo |
| 3 | 5 | + | PDP PE 16:0 | 250x | 18:2 PG | 250x | | | HDL (18:2 PG) NP with Apo |
| 4 | 5 | + | PDP PE 16:0 | 250x | 18:2 PG | 125x | Cardiolipin | 125x | HDL (cardiolipin + 18:2 PG) NP with Apo |
| 5 | 5 | + | PDP PE 18:1 | 250x | DPPC | 250x | | | HDL PDP PE 18:0 NP with Apo |

TABLE 2

Hydrodynamic diameter zeta potential of HDL NP containing cardiolipin and 18:2 PG as outer lipids (#4 in Table 1). The value for the zeta potential indicates that the particle is stable.

| Technique | Characteristic | Average value | Standard deviation |
|---|---|---|---|
| Dynamic light scattering (DLS) | Hydrodynamic diameter [nm] | 19.8 | 3.2 |
| Zeta potential [mV] | Stability | −77.0 | 3.3 |

Experiment: We tested the LPS-induced immune response in human immune cells using THP1-XBlue™-MD2-CD14 cells. THP1 is human monocytic cell line derived from an acute monocytic leukemia patient. THP1-XBlue™-MD2-CD14 cells stably express the human proteins MD2 and CD14, which are involved in LPS-induced cell signaling through the toll-like receptor 4 (TLR4). Overexpression of these two proteins increases the response of THP1 cells to the LPS. The cells also encode an NF-κB/AP-1-inducible SEAP (secreted embryonic alkaline phosphatase) reporter gene. Upon TLR4 stimulation in THP1-XBlue™-MD2-CD14 cells by LPS, a signaling cascade leads to activation of NF-κB and AP-1 and therefore production of SEAP, which is easily detectable in the conditioned cell culture media.

Figure 2A:
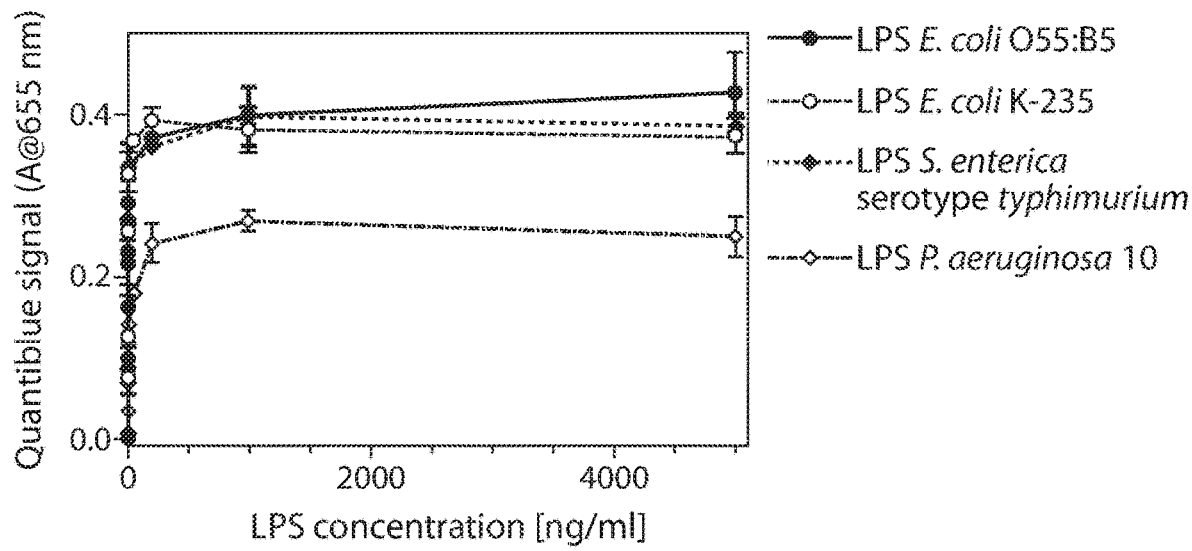
FIGS. 2A-2B.
Figure 2B:
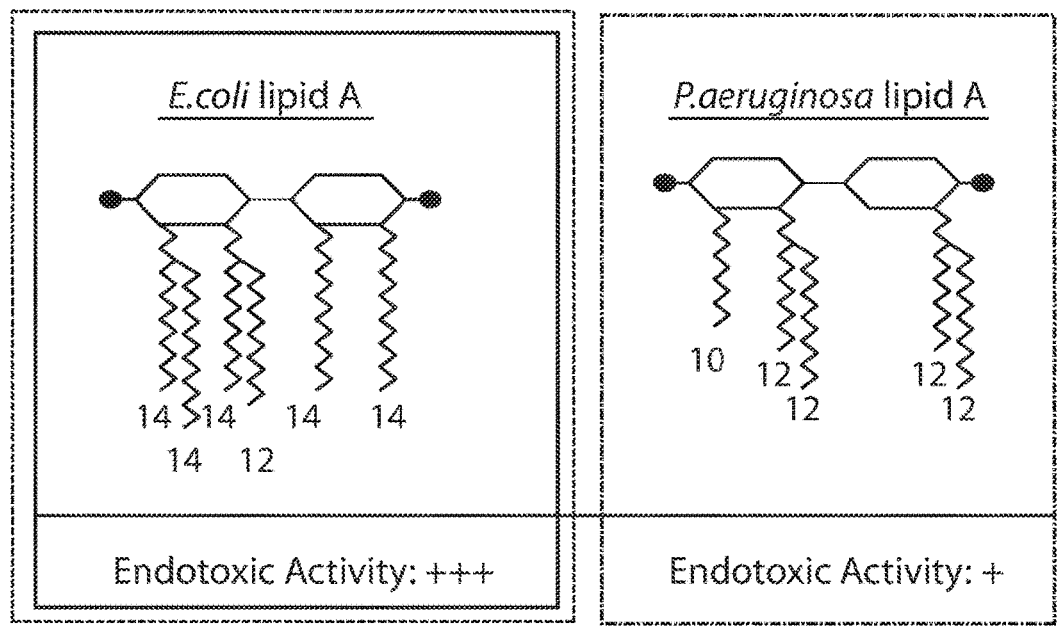

Results: It was found that treatment of THP1-XBlue™-MD2-CD14 cells with increasing LPS concentrations leads to increasing immune response (see FIG. 2). The extent to which LPS derived from different bacterial species induces an immune response in THP1-XBlue™-MD2-CD14 cells is consistent with the activities of these different LPS species that were reported in the literature (see FIG. 2). Different HDL NP constructs at a concentration of 10 nM can partially protect THP1-XBlue™-MD2-CD14 cells from an LPS-induced immune response (activation of NF-κB/AP-1-pathway) (see FIG. 3).

Figure 5:
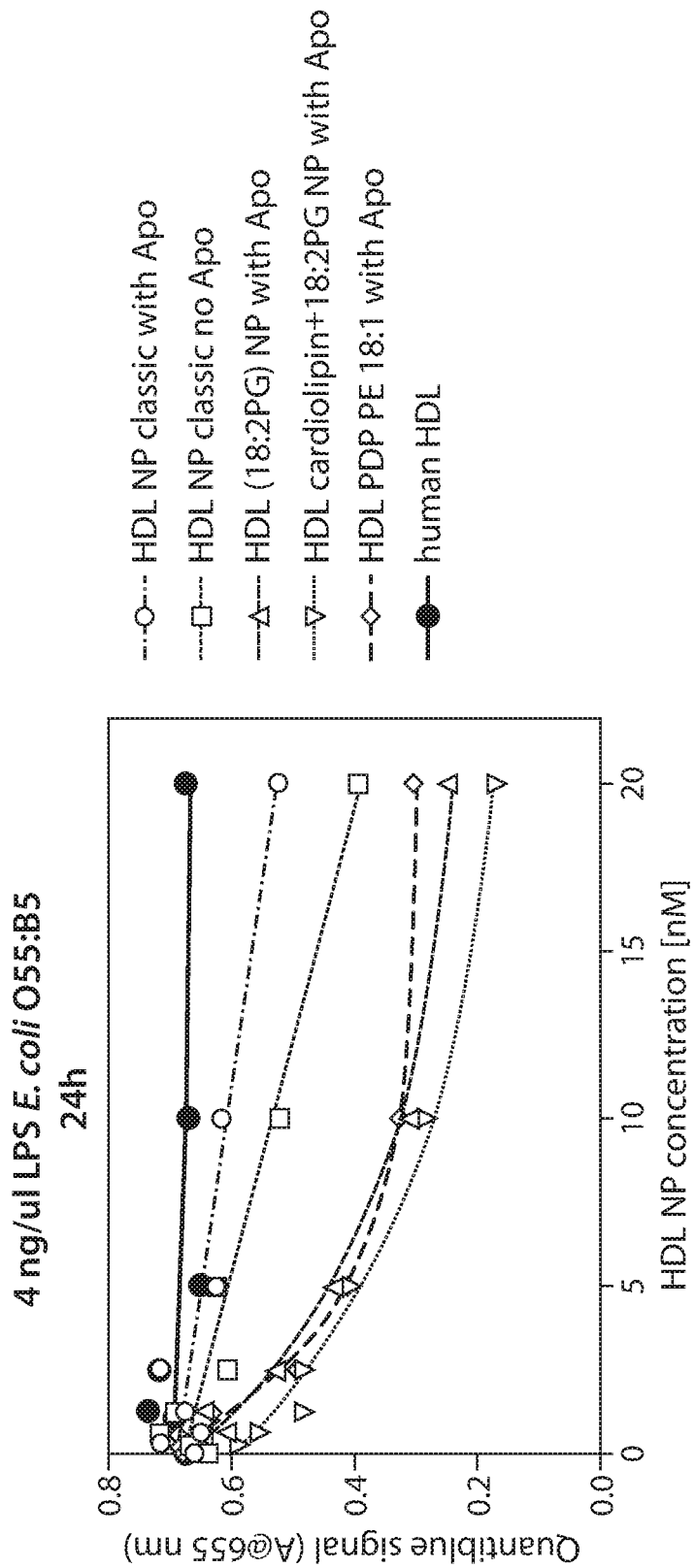
FIG. 5 shows THP1-XBlue™-MD2-CD14 cells treated with 4 ng/ml LPS derived from $E.\ coli$ O55:B5 and increasing concentrations of HDL NP/human HDL, and incubated for 24 h at 37° C. Activity of the secreted embryonic alkaline phosphatase was assessed using a Quantiblue-based assay.
Figure 6:
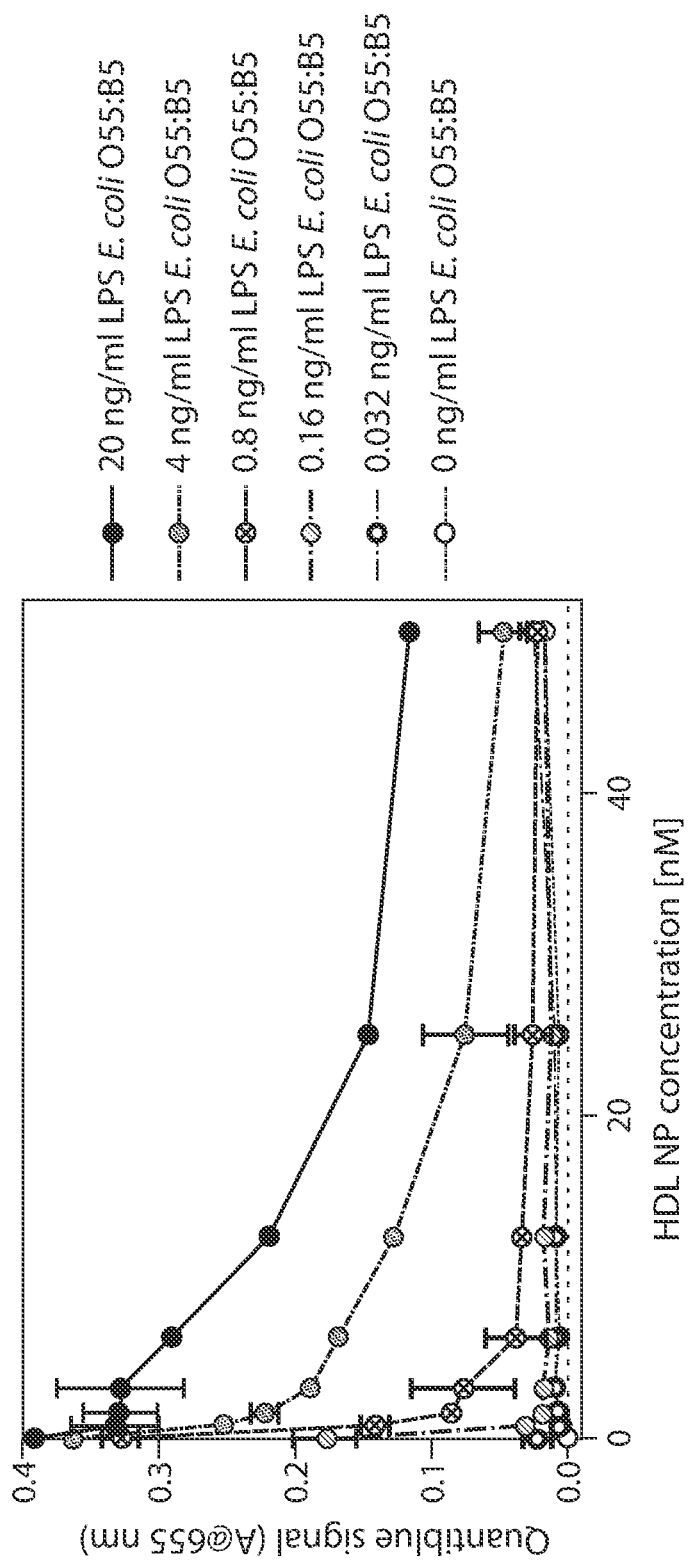
FIG. 6 shows THP1-XBlue™-MD2-CD14 cells treated with LPS derived from $E.\ coli$ O55:B5 at the indicated concentration and increasing concentrations of HDL NP constructs number 4 (see Table 1), and incubated for 24 h at 37° C. Activity of the secreted embryonic alkaline phosphatase was assessed using a Quantiblue-based assay.

Different HDL NP constructs protect THP1-XBlue™-MD2-CD14 cells from an LPS-induced immune response (activation of NF-κB/AP-1-pathway) in a dose-dependent matter: the more HDL NP present, the more the LPS-induced immune response is repressed (see FIG. 5 and FIG. 6).

Figure 3:
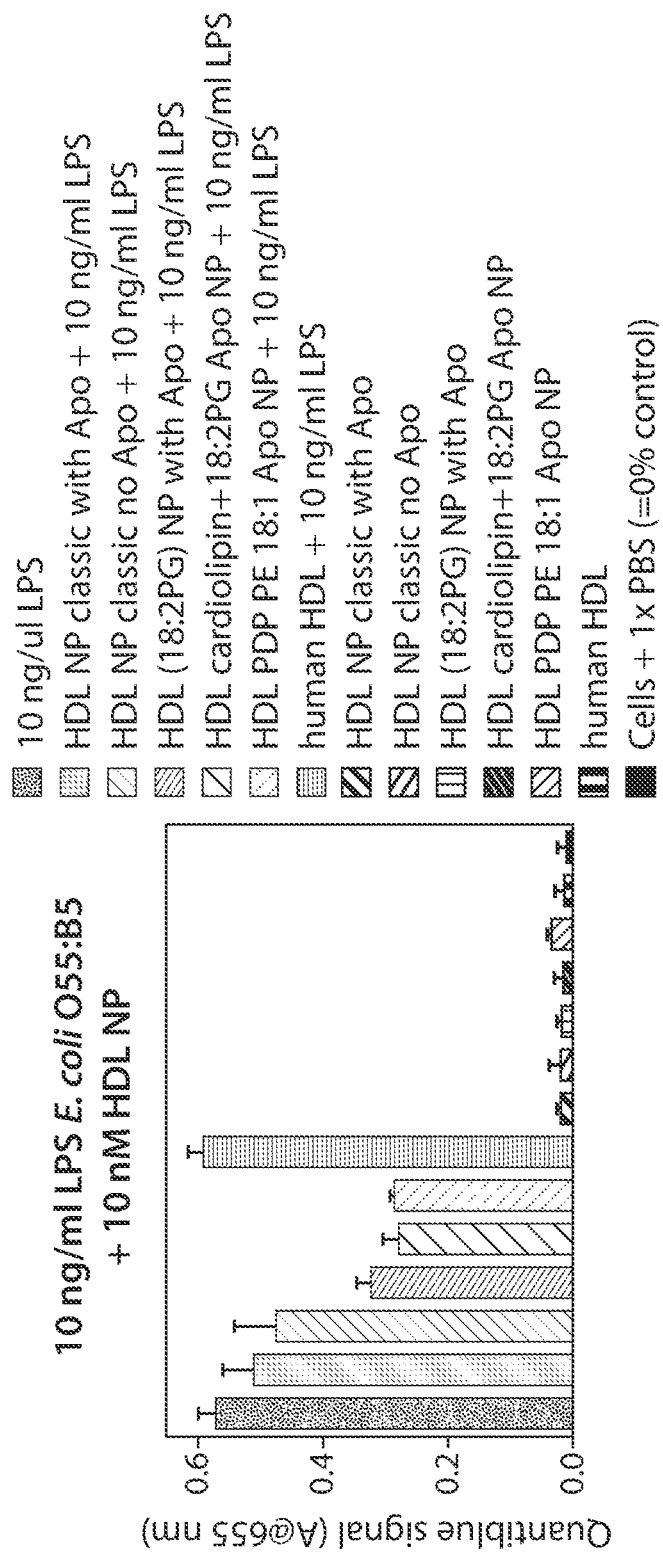
FIG. 3 shows THP1-XBlue™-MD2-CD14 cells treated with 10 ng/ml LPS derived from $E.\ coli$ O55:B5, with both LPS and 10 nM HDL NP/human HDL (hHDL), with HDL NP/hDHL and PBS or with PBS only, respectively, and incubated for 24 h at 37° C. Concentration of human HDL was based on Apolipoprotein content. Activity of the secreted embryonic alkaline phosphatase was assessed using a Quantiblue-based assay.
Figure 4:
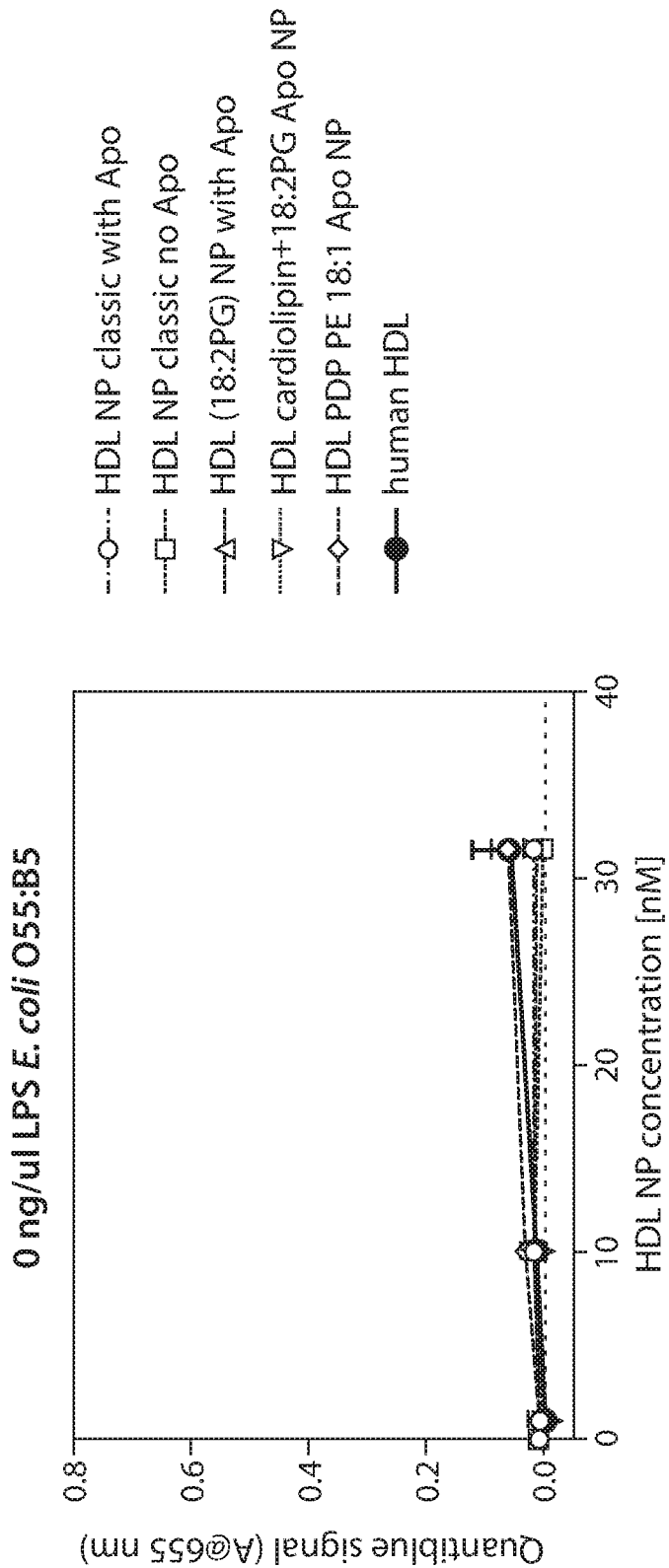
FIG. 4 shows THP1-XBlue™-MD2-CD14 cells treated with increasing concentrations of HDL NP/human HDL and incubated for 24 h at 37° C. Activity of the secreted embryonic alkaline phosphatase was assessed using a Quantiblue-based assay.
Figure 7:
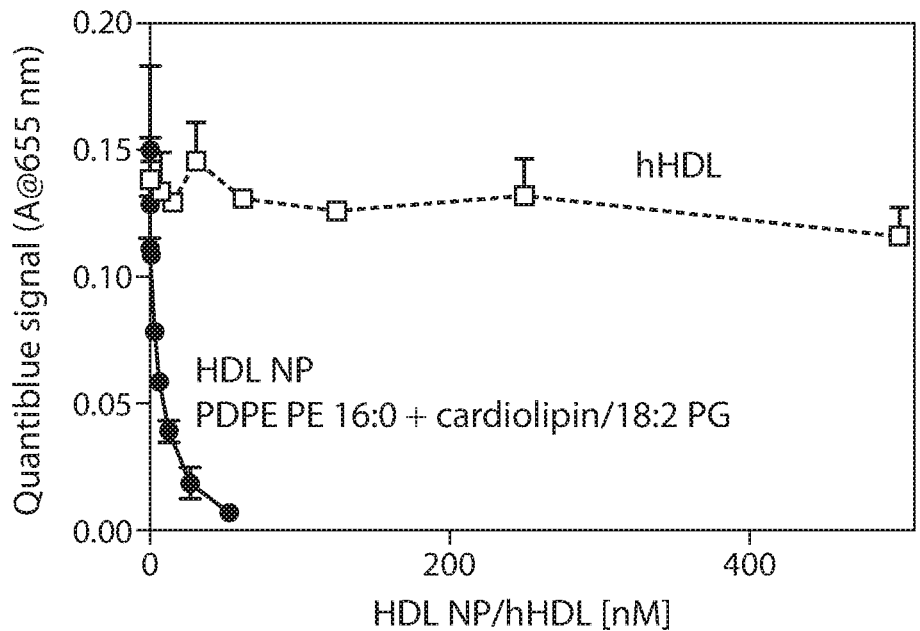
FIG. 7 shows THP1-XBlue™-MD2-CD14 cells treated with 1 ng/ml LPS derived from $E.\ coli$ O55:B5 and increasing concentrations of HDL NP construct number 4 (see Table 1) or human HDL, respectively. Cells were then incubated for 24 h at 37° C. Afterward, activity of the secreted embryonic alkaline phosphatase was assessed using a Quantiblue-based assay.

It was also found that two specific HDL NP constructs (#4 and 5, see Table 1) work particularly well in protecting THP1-XBlue™-MD2-CD14 cells from LPS-induced immune response (activation of NF-κB/AP-1-pathway) (see FIG. 3). However, the different HDL NP constructs themselves do not elicit a significant immune response at a concentration of up to 30 nM (activation of NF-κB/AP-1-pathway) in THP1-XBlue™-MD2-CD14 cells (see FIG. 3 and FIG. 4). HDL NP construct #4 (see Table 1) was superior to human HDL in preventing an LPS-induced immune response (activation of NF-κB/AP-1-pathway) in THP1-XBlue™-MD2-CD14 cells (see FIG. 2 and FIG. 7).

Timing was also investigated. The late addition of HDL NP to cells already incubated with LPS still resulted in partial suppression of the LPS-induced immune response (activation of NF-κB/AP-1-pathway) in THP1-XBlue™-MD2-CD14 (see FIG. 8).

Figure 8:
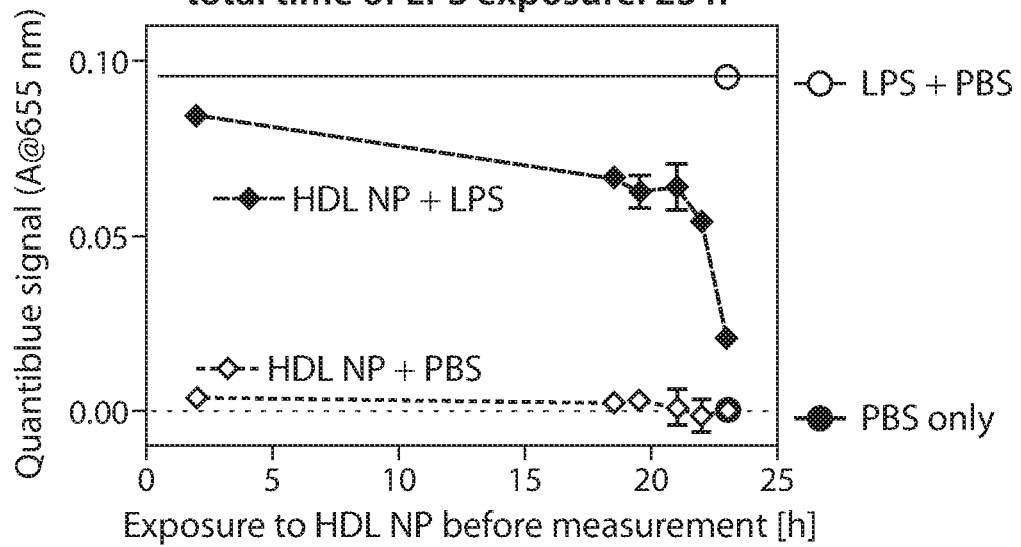
FIG. 8 shows THP1-XBlue™-MD2-CD14 cells treated with both 1 ng/ml LPS derived from $E.\ coli$ O55:B5 and 10 nM of HDL NP construct number 4 (see Table 1), or just with LPS or just with HDL NP. HDL NP were added to the cells between 0 and 21 h after LPS addition. Cells were incubated for a total of 23 h after LPS addition at 37° C. Activity of the secreted embryonic alkaline phosphatase was assessed using a Quantiblue-based assay. The total time HDL NP were co-incubated with LPS before quantification of the LPS-induced immune response was plotted on the x axis.
Figure 9A:
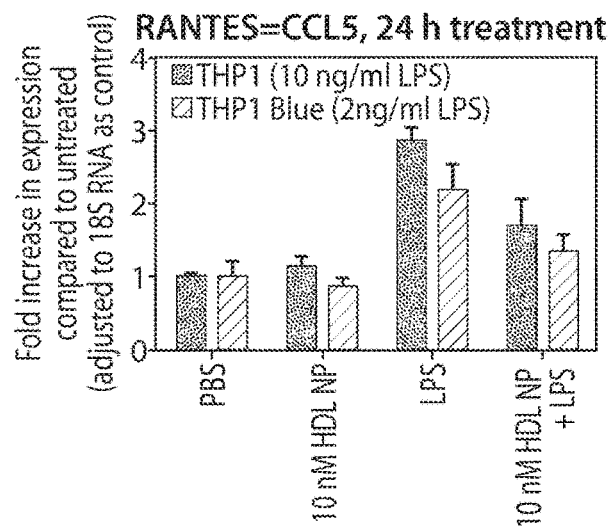
FIGS. 9A-9C show THP1-XBlue™-MD2-CD14 and THP1 cells treated with 2 ng/ml (THP1-XBlue™-MD2-CD14) or 10 ng/ml (THP1) LPS derived from $E.\ coli$ O55:B5 and 10 nM of HDL NP construct number 4 (see Table 1), or just with LPS or just with HDL NP. Cells were incubated for 24 h after LPS addition at 37° C. The RNA was isolated, and the expression levels of the genes for RANTES (FIG. 9A), IL-8 (FIG. 9B) and IL-1beta (FIG. 9C) were analyzed using real time PCR.
Figure 9B:
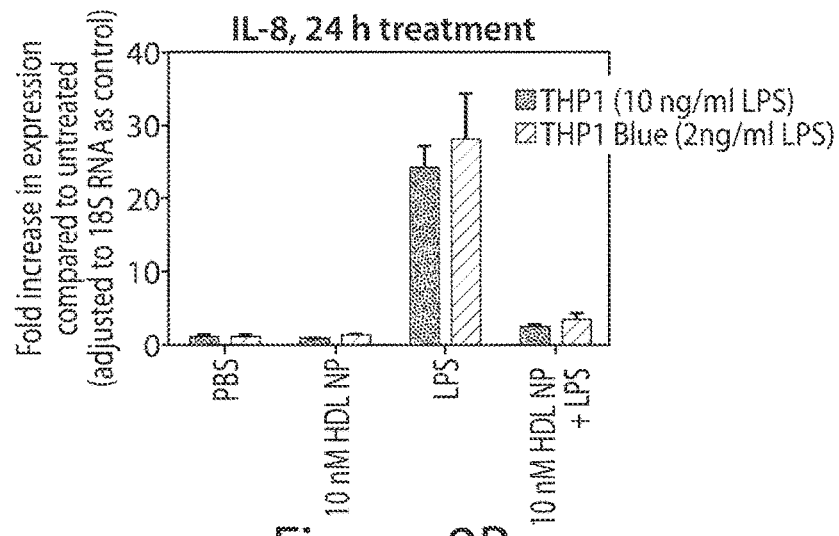
Figure 9C:
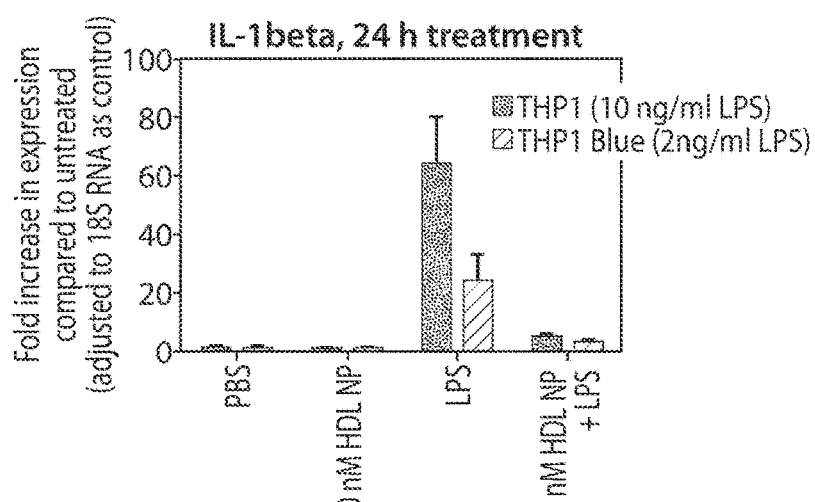
Figure 10A:
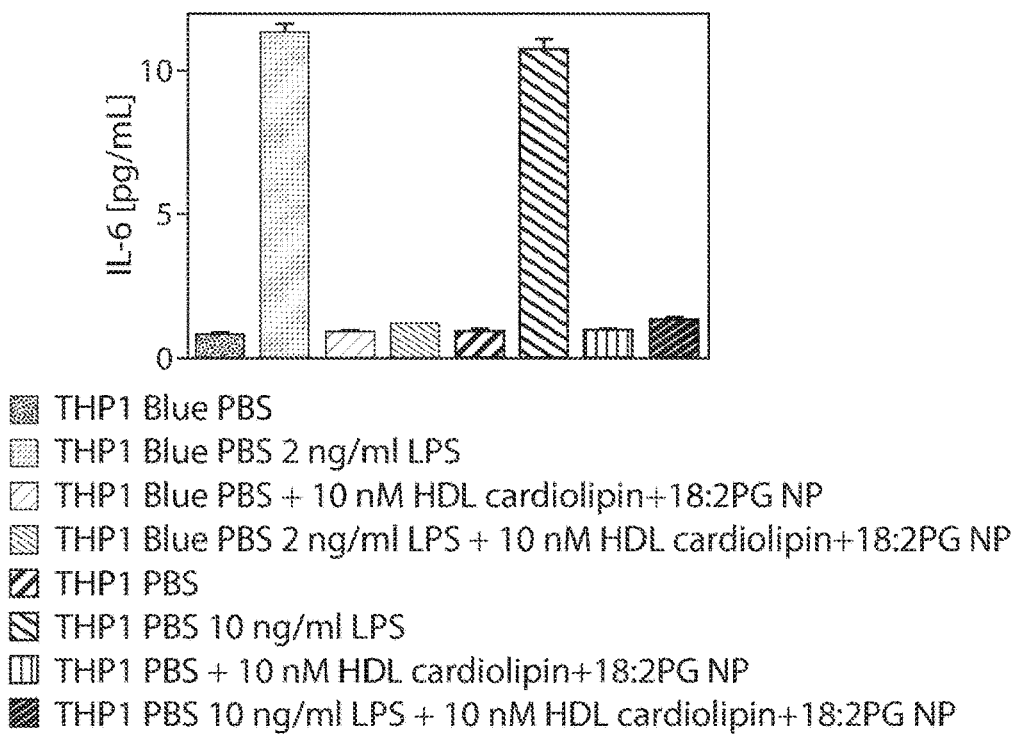
FIGS. 10A-10B.
Figure 10B:
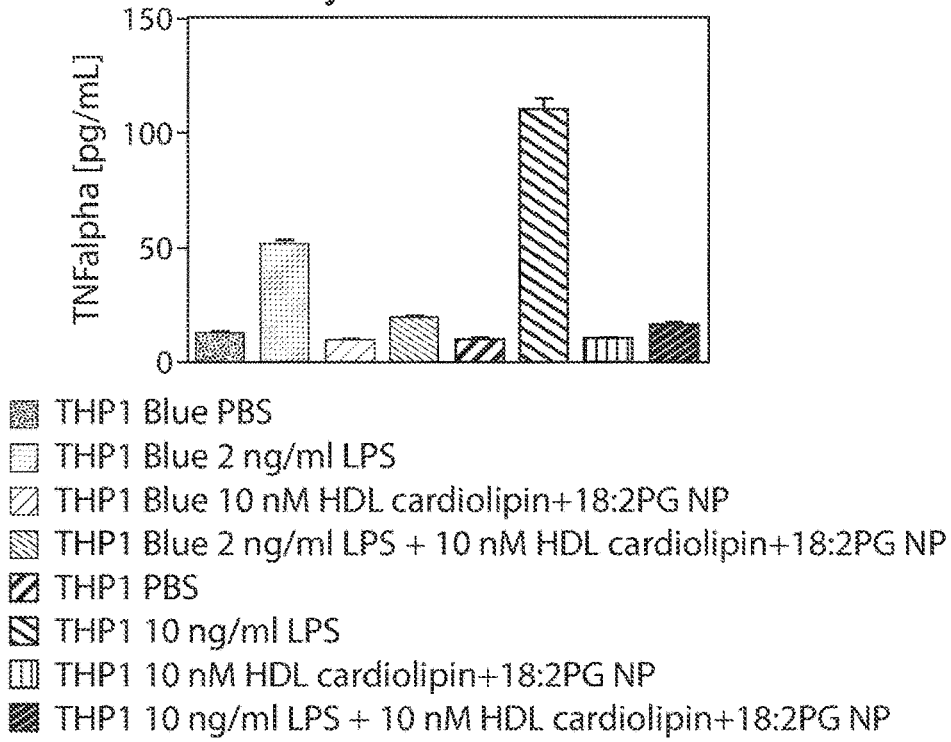

It was determined that HDL NP suppress the LPS-induced increase in expression of genes for inflammatory cytokines "regulated on activation, normal T cell expressed and secreted" (RANTES), interleukin 8 (IL-8) and interleukin 1 beta (IL-1beta), both in THP1-XBlue™-MD2-CD14, as well as regular THP1 cells that do not overexpress MD2, CD14 and the reporter protein secreted embryonic alkaline phosphatase (see FIG. 8). HDL NP also suppress the LPS-induced increase in protein levels of inflammatory cytokines interleukin 6 (IL-6) and tumor necrosis factor alpha (TNF alpha), both in THP1-XBlue™-MD2-CD14, as well as regular THP1 cells that do not overexpress MD2, CD14 and the reporter protein secreted embryonic alkaline phosphatase (see FIG. 9).

Example 2

HDL NP Reduce LPS-Induced Immune Response in Human Blood

Experiment: The LPS-induced immune response was also tested in human whole blood. The data suggest that the HDL NP also suppress a LPS-induced immune response in primary cells.

Figure 11A:
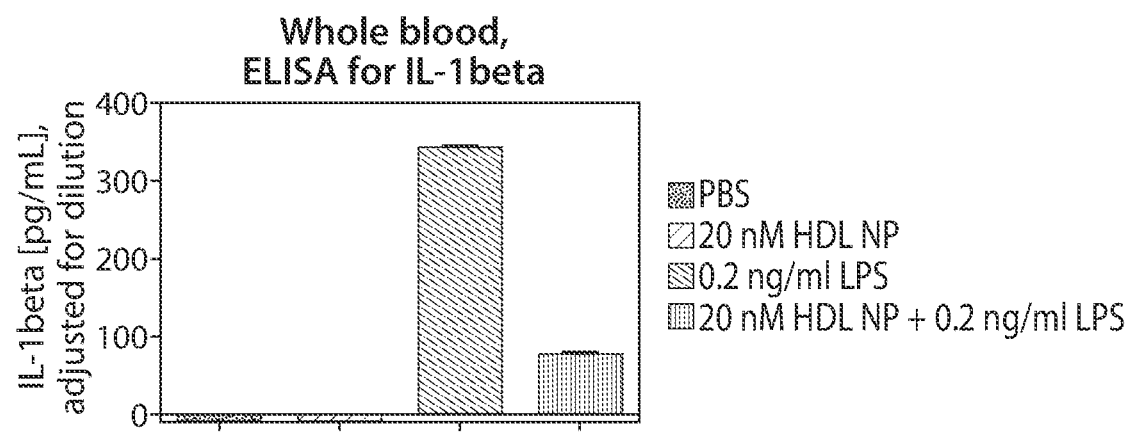
FIGS. 11A-11C show human blood from a healthy volunteer treated with 0.2 ng/ml LPS derived from $E.\ coli$ O55:B5 and 20 nM of HDL NP construct number 4 (see Table 1), or just with LPS or just with HDL NP. Cells were incubated for 18 h after LPS addition at 37° C. Cytokine levels of IL-1beta (FIG. 11A), IL-8 (FIG. 11B), and TNF-alpha (FIG. 11C) in the cell supernatant were analyzed using an enzyme-linked immunosorbent assay (ELISA).
Figure 11B:
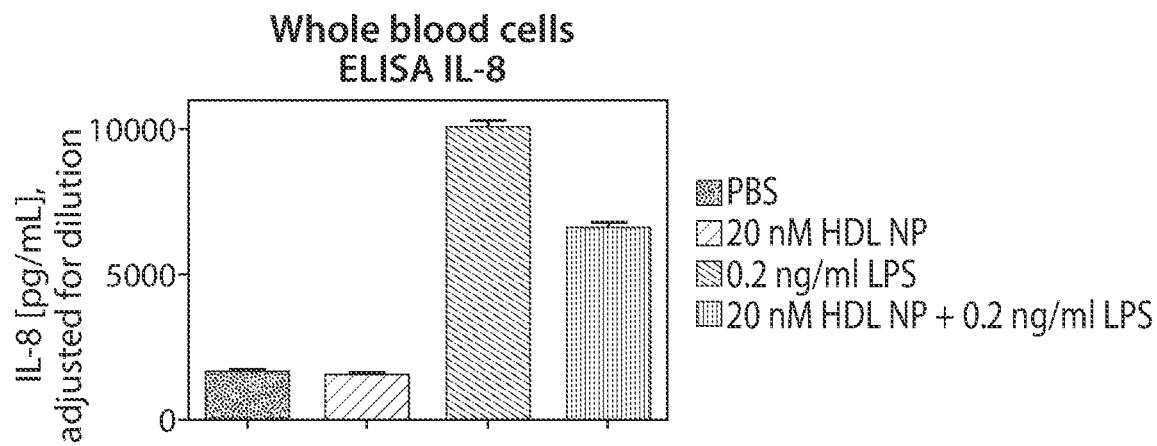
Figure 11C:
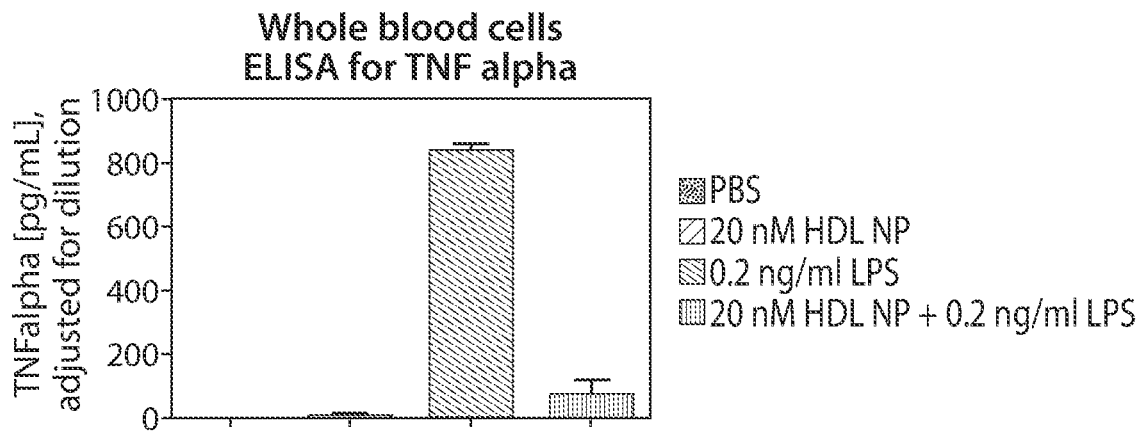

Results: It was found that HDL NP suppresses the LPS-induced increase in protein levels of inflammatory cytokines IL-8, IL-1beta and TNF-alpha (see FIG. 11).

We claim:

1. A method for decreasing the severity of an endotoxin mediated immune response, comprising
    contacting an immune cell that has been exposed to an endotoxin with a high density lipoprotein (HDL) nanoparticle (HDL-NP), wherein the HDL-NP has a zeta potential of less than −30 mV, wherein the HDL-NP comprises a core surrounded by a lipid layer shell and an apolipoprotein, wherein the lipid layer includes at least one molecule of dipalmitoylphosphatidylcholine (DPPC) in an effective amount to decrease the severity of an endotoxin mediated immune response relative to an endotoxin mediated immune response in the absence of the HDL-NP, and wherein the HDL-NP lipid layer shell comprises an inner surface and an outer surface, wherein the lipids in the outer surface of the shell are comprised of 18:2 PG.

2. A method for treating sepsis, comprising
    administering to a subject having sepsis a high density lipoprotein (HDL) nanoparticle (HDL-NP), wherein the HDL-NP is less than 30 nm in diameter and comprises a core surrounded by a lipid layer shell and an apolipoprotein, wherein the lipid layer shell includes at least one molecule of Dipalmitoylphosphatidylcholine (DPPC) in an effective amount to treat sepsis, and wherein the HDL-NP lipid layer shell comprises an inner surface and an outer surface, wherein the lipids in the outer surface of the shell are comprised of 18:2 PG.

3. A method for treating sepsis, comprising
    administering to a subject having sepsis a high density lipoprotein (HDL) nanoparticle (HDL-NP), wherein the HDL-NP comprises a core surrounded by a lipid layer shell and an apolipoprotein, and wherein the HDL-NP is administered in a HDL sub-therapeutic dose effective to treat sepsis, wherein the HDL-NP in the HDL sub-therapeutic dose is less than a molar equivalent of the free HDL or recombinant HDL, or wherein the HDL sub-therapeutic dose does not result in a therapeutic response for free HDL or recombinant HDL, and wherein the HDL-NP lipid layer shell comprises an inner surface and an outer surface, wherein the lipids in the outer surface of the shell are comprised of 18:2 PG.

4. The method of claim 1, wherein a therapeutic protein is bound to at least the outer surface of the shell.

5. The method of claim 1, wherein the lipid layer is a lipid bilayer.

6. A method for decreasing the severity of an endotoxin mediated immune response, comprising
    contacting an immune cell that has been exposed to an endotoxin with a high density lipoprotein (HDL) nanoparticle (HDL-NP), wherein the HDL-NP has a zeta potential of less than −30 mV, wherein the HDL-NP comprises a core surrounded by a lipid layer shell and an apolipoprotein, and wherein the lipid layer includes at least one molecule of cardiolipin, phosphatidylethanolamine (PE), dipalmitoylphosphatidylcholine (DPPC), and phosphatidylglycerol (PG), in an effective amount to decrease the severity of an endotoxin mediated immune response relative to an endotoxin mediated immune response in the absence of the HDL-NP, wherein the lipid layer shell has an inner surface and an outer surface, wherein at least 80% of the lipids in the outer surface of the shell are PG or cardiolipin, and wherein the HDL-NP lipid layer shell comprises an inner surface and an outer surface, wherein the lipids in the outer surface of the shell are comprised of 18:2 PG.

7. The method of claim 6, wherein at least 95% of the lipids in the outer surface of the shell are PG or cardiolipin.

8. The method of claim 1, wherein the lipid layer comprises phospholipids, unsaturated lipids, saturated lipids, and/or therapeutic lipids.

9. The method of claim 1, wherein the core comprises an inorganic material.

10. The method of claim 9, wherein the inorganic material is gold.

11. The method of claim 1, wherein the lipid layer further includes at least one molecule of phosphatidylethanolamine (PE).

12. The method of claim 1, wherein the HDL-NP has a zeta potential of −60 mV to −100 mV.

13. The method of claim 2, wherein the core comprises an inorganic material.

14. The method of claim 2, wherein the inorganic material is gold.

15. The method of claim 2, wherein the HDL-NP is 10-30 nm in diameter.

16. The method of claim 3, wherein the core comprises an inorganic material.

17. The method of claim 3, wherein the inorganic material is gold.

18. The method of claim 3, wherein the lipid layer shell is a lipid bilayer.

19. The method of claim 1, wherein the core comprises inorganic material, and the excess of lipid in the outer surface of the lipid layer shell to inorganic material in the core is at least 250-fold.

20. The method of claim 1, wherein the core comprises inorganic material, and the excess of lipid in the outer surface of the lipid layer shell to inorganic material in the core is at least 125-fold.

21. The method of claim 2, wherein the core comprises inorganic material, and the excess of lipid in the outer surface of the lipid layer shell to inorganic material in the core is at least 125-fold.

22. The method of claim 3, wherein the core comprises inorganic material, and the excess of lipid in the outer surface of the lipid layer shell to inorganic material in the core is at least 125-fold.

23. The method of claim 6, wherein the core comprises inorganic material, and the excess of lipid in the outer surface of the lipid layer shell to inorganic material in the core is at least 125-fold.

* * * * *